US011813297B2

(12) United States Patent
Allonsius et al.

(10) Patent No.: US 11,813,297 B2
(45) Date of Patent: Nov. 14, 2023

(54) PROBIOTIC *LACTOBACILLUS CASEI* STRAIN AND ITS USES

(71) Applicants: Katholieke Universiteit Leuven, KU Leuven R&D, Leuven (BE); Universiteit Antwerpen, Antwerp (BE)

(72) Inventors: Camille Allonsius, Antwerp (BE); Ilke De Boeck, Buggenhout (BE); Stijn Wittouck, Berchem (BE); Sander Wuyts, Hemiksem (BE); Sarah Lebeer, Mortsel (BE); Peter Hellings, Bertem (BE)

(73) Assignees: Katholieke Universiteit Leuven, KU Leuven R & D, Leuven (BE); Universiteit Antwerpen, Antwerp (BE)

( * ) Notice: Subject to any disclaimer, the term of this patent is extended or adjusted under 35 U.S.C. 154(b) by 96 days.

(21) Appl. No.: 16/496,719

(22) PCT Filed: Mar. 23, 2018

(86) PCT No.: PCT/EP2018/057497
§ 371 (c)(1),
(2) Date: Sep. 23, 2019

(87) PCT Pub. No.: WO2018/172537
PCT Pub. Date: Sep. 27, 2018

(65) Prior Publication Data
US 2021/0128648 A1 May 6, 2021

(30) Foreign Application Priority Data
Mar. 23, 2018 (EP) ..................................... 17162658

(51) Int. Cl.
*A61K 35/747* (2015.01)
*A23L 33/135* (2016.01)
*C12N 1/20* (2006.01)

(52) U.S. Cl.
CPC .......... *A61K 35/747* (2013.01); *A23L 33/135* (2016.08); *C12N 1/20* (2013.01); *C12Y 111/01006* (2013.01)

(58) Field of Classification Search
CPC ..... A23L 33/135; A61K 35/747; A61K 38/44; A61K 35/744; A61K 35/741; C12N 1/205; C12R 1/245; C12R 2001/245; C12Y 111/01006
See application file for complete search history.

(56) References Cited

U.S. PATENT DOCUMENTS

| 4,347,240 | A | 8/1982 | Mutai | |
|---|---|---|---|---|
| 8,372,392 | B2* | 2/2013 | Chang | ........... A23L 33/135 424/93.45 |

FOREIGN PATENT DOCUMENTS

| EP | 1661982 A1 | 7/2004 |
|---|---|---|
| WO | 03010299 A1 | 2/2003 |

OTHER PUBLICATIONS

LeBlanc et al., Use of superoxide dismutase and catalase producing lactic acid bacteria in TNBS induced Crohn's disease in mice., Journal of Biotechnology, vol. 151, Issue 3, pp. 287-293 (Year: 2011).*
Probiotics for the airways: Potential to improve epithelial and immune homeostasis, Allergy, p. 1954-1963. (Year: 2018).*
Ouwehand, et al., "Probiotics: An overview of beneficial effects", Antonie Van Leeuwenhoek, Springer, Dordrecht; NL, vol. 82, No. 1-2, Aug. 1, 2002 (Aug. 1, 2002), pp. 279-289, XP002461453.
Jin-Eung Kim, et al., "Use of selected lactic acid bacteria in the eradication of Helicobacter pylori infection", The Journal of Microbiology, vol. 52, No. 11, Nov. 1, 2014 (Nov. 1, 2014), pp. 955-962, XP055200783.
Ianniello R. G., et al., "Aeration and supplementation with heme and menaquinone affect survival to stresses and antioxidant capability of Lactobacillus caseistrains", LWT—Food Science and Technology Mar. 1, 2015 Academic Press GBR, vol. 60, No. 2, Mar. 1, 2015 (Mar. 1, 2015), pp. 817-824, XP002773325.
Kang, et al., "Complete Genome Sequence of Lactobacillus casei LCS, a Potential Probiotics for Atopic Dermatitis", Frontiers in Immunology, vol. 8, Apr. 7, 2017 (Apr. 7, 2017), XP55390835.
Bankevich, et al., "SPAdes: A New Genome Assembly Algorithm and Its Applications to Single-Cell Sequencing", Journal of Computational Biology, vol. 19, No. 5, pp. 455-477, 2012.
Wuyts, et al., "Large-Scale phylogenomics of the Lactobacillus casei group highlights taxonomic inconsistencies and Yeveals novel clade-associated features", MSYSTEMS, vol. 2, No. 4, Aug. 22, 2017 (Aug. 22, 2017), pp. e00061-e00017, XP055465954.

(Continued)

*Primary Examiner* — Taeyoon Kim
*Assistant Examiner* — Tiffany M Gough
(74) *Attorney, Agent, or Firm* — DINSMORE & SHOHL LLP

(57) ABSTRACT

The present invention is directed to a novel isolated bacterial strain of the *Lactobacillus casei* (*L. casei*) species. More in particular, the strain of the *Lactobacillus casei* species deposited under accession number LMG P-30039. The present invention further relates to the novel *L. casei* strain for use in the treatment and/or prevention of infections and/or immune-related diseases. Also the use of the isolated novel *L. casei* strain or a composition comprising said strain as an adjuvant to promote an immune response during vaccination is disclosed. Further, the use of said novel *L. casei* strain or a composition comprising said strain in personal hygiene industry, cleaning industry, biomass production, air purification and food industry is disclosed. In another aspect of the present invention, the use of a *L. casei* species that has a whole genome G/C content of at least 47.5% and expresses one or more catalase genes or a composition comprising one or more of said *L. casei* species in personal hygiene industry, cleaning industry, biomass production, air purification and food industry is disclosed.

3 Claims, 13 Drawing Sheets

(56) References Cited

OTHER PUBLICATIONS

Steidler, et al., Mucosal delivery of murine interleukin-2 (IL-2) and IL-6 by recombinant strains of Lactococcus lactis coexpressing antigen and cytokine. Infect. Immun., 1998; 66:3183-9.
Medaglini, et al., Mucosal and systemic immune responses to a recombinant protein expressed on the surface of the oral commensal bacterium *Streptococcus gordonii* after oral colonization. Proc. Natl. Acad. Sci. USA, 1995;92:6868-72.
Rowland, et al., "Toxicology of the colon: role of the intestinal microflora", In: Gibson G.R. (ed). Human colonic bacteria: role in nutrition, physiology and pathology, 1995, pp. 155-174. Boca Raton CRC Press.
Walker, "New strategies for using mucosal vaccination to achieve more effective immunization", Vaccine, 1994; 12:387-400.
Seemann, "Prokka: rapid prokaryotic genome annotation", Bioinformatics, vol. 30, No. 14, pp. 2068-2069, 2014.
Arai Ki, et al., Coordinators of immune and inflammatory responses. Annu Rev Biochem 1990;59:783-836.
McGee, et al., "A synergistic relationship between TNF-alpha, IL-1 beta, and TGF-beta 1 on IL-6 secretion by the EC-6 intestinal epithelial cell line", Immunology Sep. 1995;86(1) :6-11.
Wu, et al., Transfection of ovarian cancer cells with tumour necrosis factor alpha (TNF-alpha) antisense mRNA abolishes the proliferative response to interleukin-1 (IL-1) but not TNF-alpha. Gynecol Oncol Apr. 1994; 53(1):59-63.
Crabbe, et al., "The normal microbial flora as a major stimulus for proliferation of plasma cells synthesizing IgA in the gut. The germ free intestinal tract", Into. Arch. Allergy Appl Immunol, 1968; 34: 362-75.
Chauviere, et al., "Adherence of human Lactobacillus acidophilus strains LB to human enterocyte-like Caco-2 cells", J Gen. Microbiol 1992; 138: 1689-1696.
Bachwich, et al., "Tumor necrosis factor stimulates interleukin-1 and prostaglandin E2 production in resting macrophages", Biochem Biophys Res Commun Apr. 14, 1986;136(1):94-101.
Cicco, et al., "Inducible production of interleukin-6 by human polymorphonuclear neutrophils: role of granulocyte-macrophage colony-stimulating factor and tumor necrosis factor-alpha", Blood May 15, 1990;75(10) :2049-52.
Mangan, et al., "Lipopolysaccharide, tumor necrosis factor-alpha, and IL-1 beta prevent programmed cell death (apoptosis) in human peripheral blood monocytes", J Immunol Mar. 1, 1991;146(5):1541-6.
Dinarello, et al., "New concepts on the pathogenesis of fever", Rev Infect Dis Jan.-Feb. 1988;IO(I):168-89.
Dekker, et al., "Sensitive pulsed amperometric detection of free and conjugated bile acids in combination with gradient reversed-phase HPLC", Chromatographia 1991; 31(11/12): 549-553.
Tagg, et al., "Bacteriocins of Gram positive bacteria", Bacteriol Rev. 1976; 40: 722-756.
Kawakami, et al., "A group of bactericidal factors conserved by vertebrates for more than 300 million years", J Immunol May 1984;132(5):2578-81.
Mestan, et al., "Antiviral effects of recombinant tumour necrosis factor in vitro", Nature Oct. 3-Nov. 5, 1986;323(6091):816-9.
Ferrante, et al., "Effects of tumour necrosis factor alpha and interleukin-1 alpha and beta on human neutrophil migration, respiratory burst and degranulation", Int Arch Allergy Appl Immun.ol 1988;86(1):82-91.
Gatanaga, et al., "Purification and characterization of an inhibitor (soluble tumor necrosis factor receptor) for tumor necrosis factor and lymphotoxin obtained from the serum ultrafiltrates of human cancer patients", Proc Natl Acad Sci US A Nov. 1990;87(22):8781-4.
Gurevich, et al., "QUAST: quality assessment tool for genome assemblies", Bioinformatics, vol. 29, No. 8, pp. 1072-1075, 2013.
Donnelly RP., et al., "Differential regulation of IL-production in human monocytes by IFN-gamma and IL-4", J Immunol Jul. 15, 1990; 145(2):569-75.

Wahl SM., et al., "IFN-gamma inhibits inflammatory cell recruitment and the evolution of bacterial; cell wall-induced arthritis", J Immunol Jan. 1, 1991;146(1):95-100.
Schmitt, et al., "The immunostimulatory function of IL-12 in T-helper cell development and its regulation by TGF-beta, IFN-gamma and IL-4", Chem Immunol 1997;68:70-85.
Stallmach, et al., "Induction and modulation of gastrointestinal inflammation", Immunol. Today, 1998; 19 (10):438-41.
De Waal Malefyt R., et al., "Interleukin 10 (IL-10) and viral IL-10 strongly reduce antigen-specific human T cell proliferation by diminishing the antigen-presenting capacity of monocytes via down regulation of class II major histocompatibility complex expression", J Exp Med Oct. 1, 1991;174(4):915-24.
Cole, et al., "Ribosomal Database Project: data and tools for high throughput rRNA analysis", Nucleic Acids Research, vol. 42, pp. D633-D642, 2014.
Camacho, et al., "BLAST+ architecture and applications", BMC Bioinformatics, pp. 1-9, 2009.
Kagnoff, "Immunology of the intestinal tract", Gastroenterol. 1993; 105 (5): 1275-80.
Lamm, "Interaction of antigens and antibodies at mucosal surfaces", Ann. Rev. Microbial. 1997; 51: 311-40.
Raychaudhuri, "Fully mobilizing host defense: building better vaccines", Nat biotechnol., 1998; 16: 1025-31.
Page, et al., "Roary: rapid large-scale prokaryote pan genome analysis", Bioinformatics, Sequence Analysis, pp. 3691-3693, 2015.
Stamatakis, "RAxML Version 8: A tool for Phylogenetic Analysis and Post-Analysis of Large Phylogenies", Bioinformatics Advance Access, pp. 1-2, Jan. 21, 2014.
Letunic, et al., "Interactive tree of life (iTOL) v3: an online tool for the display and annotation of phylogenetic and other trees", Nucleic Acids Research, vol. 44, pp. W242-W245, 2016.
Rice, et al., "EMBOSS: The European Molecular Biology Open Software Suite", The European Molecular Biology Open Software Suite, vol. 16, No. 6, pp. 276-277, 2000.
Yu, et al., "GGTREE: an R package for visualization and annotation of physogenetic trees with their covariates and other associated data", Methods in Ecology and Evolution, pp. 1-9, 2016.
Finn, et al., "HIMMER web server: interactive sequence similarity searching", Nucleic Acid Research, vol. 39, pp. W29-W37, 2011.
Veen, et al., "The BER necessities: the repair of DNA damage in human-adapted bacterial pathogens", Nature Reviews Microbiology, vol. 13, pp. 83-94, 2015.
Richter, et al., "Shifting the genomic gold standard for the prokaryotic species definition", PNAS, vol. 106, No. 45, pp. 19126-19131, Nov. 10, 2009.
Zotta, et al., "Draft Genome Sequence of the Respiration-Competent Strain Lactobacillus casei N87", American Society for Microbiology, Genome Announcements, vol. 4 Issue 3, pp. 1-2, 2016.
Zotta, et al., "Assessment of Aerobic and Respiratory Growth in the Lactobacillus casei Group", PLOS One, vol. 9, Issue 6, pp. 1-11, Jun. 2014.
Lechardeur, et al., "Using heme as an energy boost for lactic acid bacteria", Biotechnology, Science Direct, pp. 143-149, 2011.
Pederson, et al., "Aerobic Respiration Metabolism in Lactic Acid Bacteria and Uses in Biotechnology", Annual Reviews Food Sci. Technology, pp. 37-60, 2012.
Liu, et al., "Cloning and heterologous expression of the manganese superoxide dismutase gene from Lactobacillus casei Lc18", Ann. Microbiology, pp. 129-137, 2012.
International Search Report dated Jun. 18, 2018, in reference to co-pending European Patent Application No. PCT/EP2018/057497 filed Mar. 23, 2018.
European Patent Office Search Report to co-pending European Patent Application No. EP 17162658.3.
Sun, et al., "Expanding the biotechnology potential of lactobacilli through comparative genomics of 213 strains and associated gemera", Nature Communications, pp. 1-13, 2015.

* cited by examiner

| strain | Pathogen used in spot assay | | | | | | |
|---|---|---|---|---|---|---|---|
| | E. coli | H. influenzae | M. catarrhalis | S. pneumoniae | S. aureus | Shigella flexneri | S. hyicus |
| AMBR1 | 1 | 3 | 3 | 0 | 0 | 2 | 2 |
| AMBR2 | 3 | 3 | 3 | 0 | 1 | 3 | 2 |
| AMBR3 | 0 | 3 | 3 | 0 | 0 | 2 | 1 |
| AMBR4 | 0 | 3 | 3 | 0 | 0 | 2 | 2 |
| AMBR5 | 1 | 3 | 3 | 0 | 0 | 2 | 2 |
| LGG | 1 | 2 | 3 | 0 | 0 | 3 | 3 |
| Pathogen control | 0 | 0 | 0 | 0 | 0 | 0 | 0 |

A

B

ANIb

TETRA

PROBIOTIC *LACTOBACILLUS CASEI* STRAIN AND ITS USES

FIELD OF THE INVENTION

The present invention is directed to a novel isolated bacterial strain of the *Lactobacillus casei* (*L. casei*) species. Said strain of the *Lactobacillus casei* species is deposited under accession number LMG P-30039. The novel strain is characterized by a whole genome G/C content of 48.02%, and harbours one or more catalase genes. The novel strain is further characterized by an average nucleotide identity of its genome to the genome sequence of the known *L. casei* strain ATCC 393 of 94%.

The present invention further relates to the novel *L. casei* strain for use in the treatment and/or prevention of infections and/or immune-related diseases. Also the use of the isolated novel *L. casei* strain or a composition comprising said strain as an adjuvant to promote an immune response during vaccination is disclosed. Further, the use of said novel *L. casei* strain or a composition comprising said strain in personal hygiene industry, cleaning industry, biomass production and air purification is disclosed.

In another aspect of the present invention, the use of a *L. casei* species that has a whole genome G/C content of at least 47.5% and harbours one or more catalase genes in personal hygiene industry, cleaning industry, biomass production and air purification is disclosed. Further, the use of a *L. casei* species that has a whole genome G/C content of at least 47.5%, that harbours one or more catalase genes and has robust, glycosylated, serine-rich repeat protein, single-subunit fimbriae with an average length of at least 0.4 µm, for use in personal hygiene industry, cleaning industry, biomass production, air purification and food industry is disclosed. Further, the use of a composition comprising one or more *L. casei* species in personal hygiene industry, cleaning industry, biomass production, air purification and food industry is disclosed.

BACKGROUND TO THE INVENTION

The *Lactobacillus* genus is the largest genus within the lactic acid bacteria comprising more than 200 species. Lactobacilli are naturally present in human and animal mucosal surfaces (e.g. gastro-intestinal and vaginal tract), and many food-related environments, including plants (fruits, vegetables, cereal grains), wine, milk and meat environments, where they can become dominant if able to ferment high doses of sugar with concomitant production of lactic acid and related metabolites. In microbiology textbooks, they are referred to as rod-shaped Gram-positive non-sporulating, non-motile, non-pathogenic, cytochrome-negative and catalase-negative bacteria. With their high number of GRAS (Generally Recognized As Safe) species by the FDA in the US, or QPS (Qualified Presumption of Safety) by EFSA in Europe they are currently exploited in many applications ranging from the use as starter cultures, probiotics, production of bioplastics to vaccine carriers, showing they have also have a high commercial value.

The *Lactobacillus casei* group, comprising the species *Lactobacillus casei*, *L. paracasei* and *L. rhamnosus* are among the economically most interesting groups of phylogenetically and phenotypically closely related *Lactobacillus* species. However, both the nomenclature and classification of this group are subjects of discussion. This is for example reflected in the introduction of the related species *L. zeae* in 1996 and subsequently its rejection in 2008. Furthermore, recent comparative genomics show that many strains currently labeled as *L. casei* and *L. paracasei* strains are in fact members of the same species. In addition, many new isolates are labeled as *L. casei* while they are more closely related to *L. paracasei* type strain ATCC 334 than to *L. casei* type strain ATCC 393 due to high heterogeneity in 16S rRNA genes. Thus many novel identifications are not in line with the current taxonomic classification. Different efforts have been made to facilitate the differentiation between *L. casei* group members based on the use of PCR and/or DNA-fingerprinting techniques. However, with the price reduction of whole-genome sequencing, the rising availability of public genomes (210 *L. casei* group members on 19 Feb. 2017 on NCBI) as well as new genomic-based taxonomic classification methods like ANI and TETRA, a more in-depth insight into the genetic differences, and thus the taxonomy, of *L. casei* group members can be obtained using comparative genomics.

The group contains the well-studied probiotic bacterium *L. rhamnosus* GG, as well as many strains used for food fermentations, such as the strain *L. paracasei* ATCC 334, an Emmental cheese isolate. Commercially, the microbes from this group are applied in fermented dairy products or food supplements targeted at the gastro-intestinal tract and vaginal tract, but interest is increasing to apply them in other product formulations targeting other (human and animal) body niches.

In the present invention, a novel strain of the *Lactobacillus casei* (*L. casei*) species was identified (deposited under accession number LMG P-30039, herein further also indicated as AMBR2). This strain is characterized by a high whole genome G/C content of more than 47.5%, in particular a whole genome G/C content of 48.02% and harbours at least two catalase genes. Further, said strain has an average nucleotide identity of its genome to the genome sequence of the known *L. casei* strain ATCC 393 of 94%. The LMG P-30039 strain is further also characterized in that it comprises special fimbriae with an average length of at least 0.4 µm; in particular special robust, glycosylated serine-rich, single-protein-subunit fimbriae with an average length of at least 0.4 µm. Also the use of said novel strain in medical applications, as well as in personal hygiene industry, cleaning industry, biomass production, air purification or food industry is provided.

Another aspect of the present invention, is to provide more insight into the genetic relationship of strains belonging to the *L. casei* group. In particular, by using comparative genomic approaches, a novel classification for a number of *L. casei* strains, including the *L. casei* species deposited under accession number LMG P-30039, was identified. The present invention therefore provides the use of a *Lactobacillus casei* species that has a whole genome G/C content of 48.02% and harbours one or more catalase genes in personal hygiene industry, cleaning industry, biomass production and air purification. Further, the use of a composition comprising said *L. casei* species in personal hygiene industry, cleaning industry, biomass production and air purification is disclosed.

SUMMARY OF THE INVENTION

The present invention is based on the identification of a novel isolated strain of the *Lactobacillus casei* (*L. casei*) species. Said strain has been deposited with the Belgian Co-ordinated Collection of Micro-Organisms (BCCM), Universiteit Gent, K. L. Ledeganckstraat 35, 9000 Gent, Belgium) on Feb. 21, 2017 with accession number LMG P-30039 and herein further also indicated as AMBR2 strain. Typical for this novel isolated strain of the *L. casei* species is that it has a high whole genome G/C content of 48.02%. Further, said isolated strain of the *L. casei* species harbours one or more catalase genes. In particular, said catalase genes are selected from the group comprising heme-catalase and manganese catalase. The novel isolated strain is further characterized by an average nucleotide identity to the genome sequence of the ATCC 393 *L. casei* strain of 94%. In addition, the novel isolated strain is also characterized in that it comprises special fimbriae with an average length of at least 0.4 µm; in particular special robust, glycosylated serine-rich, single-subunit fimbriae with an average length of at least 0.4 µm, thereby enhancing adhesion on epithelial cells.

In another embodiment, also a composition comprising an isolated bacterial strain of the *L. casei* species deposited under accession number LMG P-30039 is disclosed. In an even further embodiment, said composition can optionally comprise other probiotic bacteria.

The present invention is further based on the finding that the isolated strain of the *L. casei* species as deposited under accession number LMG P-30039 shows strong adhesion capacity on epithelial cells, in particular respiratory epithelial cells (cfr. niche of isolation), as also other human epithelial cells (colon and vaginal) cells. Therefore, in a further aspect, the present invention provides said isolated strain of *L. casei* species or a composition comprising said strain for use in the treatment and/or prevention of infections and/or immune-related diseases. Even further, said isolated strain of *L. casei* species or a composition comprising said strain is disclosed for use in the treatment and prevention of oronasopharyngeal infections, in particular infections of the oronasopharyngeal cavity or oral infections, more in particular upper respiratory tract infections selected from the group comprising otitis media, pharyngitis, chronic sinusitis, acute sinusitis, rhinitis, flue, mucositis, caries, gingivitis, or halitosis and the like.

In another embodiment, the novel isolated strain of *L. casei* or composition according to the present invention is disclosed for use in the treatment and/or prevention of skin infections, in particular acne vulgaris, psoriasis, burn wounds, cellulitis, impetigo, athlete's feet (tinea pedis), fungal nail infections, or warts, and the like.

In a further embodiment, the novel isolated strain of *L. casei* or a composition according to the present invention is disclosed for use in the treatment and/or prevention of mastitis.

In yet another embodiment, the present invention discloses said isolated strain of the *L. casei* species or a composition comprising said isolated strain of the *L. casei* species for use in the treatment and/or prevention of urogenital infections, in particular vaginal infections and bladder infections.

In still another embodiment, the present invention discloses an isolated strain of the *L. casei* species deposited under accession number LMG P-30039, or a composition comprising said strain for use in the treatment and/or prevention of gastro-intestinal infections, in particular colitis, stomach infections, inflammatory bowel disease, irritable bowel syndrome, and the like.

The present invention also provides the isolated strain of the *L. casei* species deposited under accession number LMG P-30039 or a composition comprising said strain for use in the treatment and/or prevention of allergic diseases. Said allergic diseases are selected from the group comprising hay fever, allergic rhinitis, allergic sinusitis, asthma, and the like.

Further, also the use of the isolated strain of the *L. casei* species deposited under accession number LMG P-30039, or a composition comprising said strain as an adjuvant to promote an immune response during vaccination is disclosed.

Based on the finding that the isolated strain of the *L. casei* species with accession number LMG P-30039 shows improved adhesion capacity to respiratory epithelial cells, the present invention also provides the use of said isolated strain or a composition comprising said strain in personal hygiene industry. In particular, the personal hygiene industry comprises production of tissues, protective masks or sprays. Even more in particular, said tissues, protective masks or sprays are directed towards the treatment and/or prevention of respiratory infections.

In another embodiment, the use of said novel isolated strain with accession number LMG P-30039 or a composition comprising said strain is disclosed in the cleaning industry, in particular in the production of a cleaning product.

In still another embodiment, the present invention provides the use of the isolated bacterial strain with accession number LMG P-30039 or the use of a composition comprising said strain in air purification, in particular in air purification filters.

In another embodiment, the present invention provides the use of the isolated bacterial strain with accession number LMG P-30039 or the use of a composition comprising said strain in biomass production.

In another embodiment, the present invention provides the use of the isolated bacterial strain with accession number LMG P-30039 or the use of a composition comprising said strain in the food industry.

Optionally, said isolated strain of the *L. casei* species with accession number LMG P-30039 or the composition comprising said novel isolated bacterial strain can be combined in combination with other probiotic bacteria.

The present invention is further based on the finding that several strains of the *L. casei* group can be categorized in a separate group using comparative genomics analyses. In particular, members of said group have a whole genome G/C content of at least 47.5% and harbour one or more, in particular two catalase genes, even more in particular members of said group harbour one or more, in particular two catalase genes selected from heme-catalase and manganese catalase. Further, members of said group have a genome with an average nucleotide identity of at least 93% to the genome sequence of the ATCC 393 *L. casei* strain. Finally, members of said group are further also characterized in that they comprise special robust, glycosylated, serine-rich, single subunit fimbriae with an average length of at least 0.4 µm. Said fimbriae are involved in tissue-specific adhesion of the species to epithelial cells, for example respiratory epithelial cells.

The present invention therefore provides a *L. casei* species for use in the treatment and/or prevention of infections and/or immune-related diseases, wherein said *L. casei* species has a whole genome G/C content of at least 47.5%, and harbours one or more catalase genes. In a further embodiment, said *L. casei* species may comprise special robust, glycosylated, serine-rich, single subunit fimbriae with an average length of at least 0.4 µm. In still a further embodiment, the present invention provides said *L. casei* species having a whole genome G/C content of at least 47.5% and harbouring one or more catalase genes for use in the treatment and/or prevention of oronasopharyngeal infections, in particular infections of the oronasopharyngeal cavity and oral infections, more in particular upper respiratory tract infections selected from the group comprising acute otitis media, pharyngitis, chronic sinusitis, acute sinusitis, rhinitis, flue, mucositis, caries, gingivitis, or halotosis and the like. In a further embodiment, said *L. casei* species may comprise special fimbriae with an average length of at least 0.4 µm; in particular special robust, glycosylated, serine-rich, single subunit fimbriae with an average length of at least 0.4 µm.

In another embodiment, the present invention provides a *L. casei* species having a whole genome G/C content of at least 47.5% and harbours one or more, in particular two catalase genes for use in the treatment and/or prevention of skin infections, in particular acne vulgaris, psoriasis, burn wounds, cellulitis, impetigo, athlete's feet (tinea pedis), fungal nail infections, or warts, and the like. In a further embodiment, said *L. casei* species may comprise special fimbriae with an average length of at least 0.4 µm; in particular special robust, glycosylated, serine-rich, single subunit fimbriae with an average length of at least 0.4 µm.

In still another embodiment, the present invention provides a *L. casei* species having a whole genome G/C content of at least 47.5% and harbouring one or more, in particular two catalase genes for use in the treatment and/or prevention of mastitis. Said *L. casei* species further may comprise special fimbriae with an average length of at least 0.4 µm; in particular special robust, glycosylated, serine-rich, single subunit fimbriae with an average length of at least 0.4 µm.

In yet another embodiment, the present invention provides a *L. casei* species having a whole genome G/C content of at least 47.5% and harbouring one or more, in particular two catalase genes for use in the treatment and/or prevention of urogenital infections, in particular vaginal infections and bladder infections. Said *L. casei* species further may comprise special fimbriae with an average length of at least 0.4 µm; in particular special robust, glycosylated, serine-rich, single subunit fimbriae with an average length of at least 0.4 µm.

In still a further embodiment, the present invention provides a *L. casei* species having a whole genome G/C content of at least 47.5% and harbouring one or more, in particular two catalase genes for use in the treatment and/or prevention of gastro-intestinal infections, in particular colitis, stomach infection, inflammatory bowel disease, irritable bowel syndrome and the like. Said *L. casei* species further may comprise special fimbriae with an average length of at least 0.4 µm; in particular special robust, glycosylated, serine-rich, single subunit fimbriae with an average length of at least 0.4 µm.

In another embodiment, the present invention provides a *L. casei* species having a whole genome G/C content of at least 47.5% and harbouring one or more, in particular two catalase genes for use in the treatment and/or prevention of immune-related diseases, in particular immune-related diseases selected from the group comprising hay fever, allergic rhinitis, allergic sinusitis, asthma, and the like. Said *L. casei* species further may comprise special fimbriae with an average length of at least 0.4 µm; in particular special robust, glycosylated, serine-rich, single subunit fimbriae with an average length of at least 0.4 µm.

The present invention further discloses the use of a *L. casei* species having a whole genome G/C content of at least 47.5% and harbouring one or more, in particular two catalase genes in personal hygiene industry. Said *L. casei* species further may comprise special fimbriae with an average length of at least 0.4 µm; in particular special robust, glycosylated, serine-rich, single subunit fimbriae with an average length of at least 0.4 µm.

Also the use of a composition comprising said *L. casei* species in personal hygiene industry is disclosed. In particular, the use of *L. casei* species having a whole genome G/C content of at least 47.5% and harbouring one or more, in particular two catalase genes or a composition comprising said *L. casei* species in the production of tissues, protective masks or sprays is disclosed. Said *L. casei* species may further comprise special robust, glycosylated, serine-rich, single subunit fimbriae with an average length of at least 0.4 µm. Even more in particular, said tissues, protective masks or sprays are directed towards the treatment and/or prevention of respiratory infections.

In another aspect, the present invention discloses the use of a *L. casei* species or a composition comprising one or more of said *L. casei* species in air purification, in particular in air purification filters, wherein said *L. casei* species has a whole genome G/C content of at least 47.5% and harbours one or more, in particular two catalase genes. Said *L. casei* species further may comprise special fimbriae with an average length of at least 0.4 µm; in particular special robust, glycosylated, serine-rich, single subunit fimbriae with an average length of at least 0.4 µm.

In a further aspect, the present invention discloses the use of a *L. casei* species or a composition comprising one or more of said *L. casei* species in the production of biomass, wherein said *L. casei* species has a whole genome G/C content of at least 47.5% and harbours one or more, in particular two catalase genes. Said *L. casei* species is further characterized in that it comprises special fimbriae with an average length of at least 0.4 µm; in particular special robust, glycosylated, serine-rich, single subunit fimbriae with an average length of at least 0.4 µm.

Further referring to the different uses of the *L. casei* species according to the present invention or the composition comprising the *L. casei* species according to the present invention, said *L. casei* species harbours one or more, in particular two catalase genes, wherein the one or more catalase genes are selected from the group comprising heme-catalase and manganese catalase. Said *L. casei* species further may comprise special fimbriae with an average length of at least 0.4 µm; in particular special robust, glycosylated, serine-rich, single subunit fimbriae with an average length of at least 0.4 µm.

In yet another embodiment of the present invention, and also referring to the different uses of the *L. casei* species or composition comprising said *L. casei* species according to the present invention, said species has a genome with an average nucleotide identity to the genome sequence of the ATCC 393 *L. casei* strain of at least 93%. Said *L. casei* species further may comprise special fimbriae with an average length of at least 0.4 µm; in particular special robust, glycosylated, serine-rich, single subunit fimbriae with an average length of at least 0.4 µm.

In still another embodiment of the present invention, and further referring to the different uses of the *L. casei* species or the composition comprising the *L. casei* species, said species shows an enhanced adhesion to epithelial cells, in particular respiratory epithelial cells, because of expression of special fimbriae. In particular, said special fimbriae of the *L. casei* species are typically characterized in that the average length of the fimbriae in a particular strain of said species is at least 0.4 µm, being robust (resistant to shear forces during centrifugation and spray drying). In a further embodiment, said fimbriae are glycosylated, serine-rich, single subunit.

In the context of the present invention, the term "average length of the fimbriae" is meant to be based on analysis through scanning electron microscopy (SEM) after washing of the bacteria with a suitable buffer (e.g. Phosphate Buffered Saline), with in-between centrifugation of the cells at min. 2000 g. The length of at least 10 fimbriae on one or two bacterial cells is carefully determined (expressed in μm) and the average is determined.

Some of the aspects of the present invention can be summarized in the following numbered embodiments:

1. An isolated bacterial strain of the *Lactobacillus casei* (*L. casei*) species, said strain deposited under accession number LMG P-30039.

2. The isolated bacterial strain according to embodiment 1, wherein said isolated bacterial strain has a whole genome G/C content of 48.02% 3. The isolated bacterial strain according to embodiment 1 or 2, wherein said isolated bacterial strain harbours one or more catalase genes.

4. The isolated bacterial strain according to embodiment 3, wherein the one or more catalase genes are selected from the group comprising heme-catalase and manganese catalase.

5. The isolated bacterial strain according to anyone of embodiments 1 to 4, wherein said isolated bacterial strain has a genome with an average nucleotide identity to the genome sequence of the ATCC393 *L. casei* strain of 94%%.

6. A composition comprising an isolated bacterial strain of the *L. casei* species according to anyone of embodiments 1 to 5.

7. The isolated bacterial strain according to anyone of embodiments 1 to 5 or the composition according to embodiment 6 for use in the treatment and/or prevention of infections or immune-related diseases.

8. The isolated bacterial strain or composition for use according to embodiment 7 wherein said infections are oronasopharyngeal infections, in particular upper respiratory tract infections selected from the group comprising otitis media, pharyngitis, chronic sinusitis, acute sinusitis, rhinitis, flue, mucositis, caries, gingivitis, or halitosis and the like.

9. The isolated bacterial strain or composition for use according to embodiment 7, wherein said infections are skin infections, in particular acne vulgaris, psoriasis, burn wounds, cellulitis, impetigo, athlete's feet (tinea pedis), fungal nail infections, or warts, and the like.

10. The isolated bacterial strain or composition for use according to embodiment 7, wherein said infections are mastitis.

11. The isolated bacterial strain or composition for use according to embodiment 7 wherein the infections are urogenital infections, in particular vaginal infections and bladder infections.

12. The isolated bacterial strain or composition according to embodiment 7 wherein the infections are gastro-intestinal infections, in particular colitis, stomach infection, inflammatory bowel disease, irritable bowel syndrome and the like.

13. The isolated bacterial strain or composition according to embodiment 7 wherein the immune-related diseases are selected from the group comprising hay fever, allergic rhinitis, allergic sinusitis, asthma, and the like.

14. Use of the isolated bacterial strain according to anyone of embodiments 1 to 5 or the composition according to embodiment 6 as an adjuvant to promote an immune response during vaccination.

15. Use of the isolated bacterial strain according to anyone of embodiments 1 to 5 or use of the composition according to embodiment 6 in personal hygiene industry, in particular in the production of tissues, protective masks or sprays.

16. Use of the isolated bacterial strain according to anyone of embodiments 1 to 5 or use of the composition according to embodiment 6 in cleaning industry, in particular in the production of a cleaning product.

17. Use of the isolated bacterial strain according to anyone of embodiments 1 to 5, or use of the composition according to embodiment 6 in air purification, in particular in air purification filters.

18. Use of the isolated bacterial strain according to anyone of embodiments 1 to 5, or use of the composition according to embodiment 6 in biomass production.

19. A *L. casei* species having a whole genome G/C content of at least 47.5% and harbouring one or more catalase genes for use in the treatment and/or prevention of infections or immune-related diseases.

20. A *L. casei* species having a whole genome G/C content of at least 47.5%, harbouring one or more catalase genes and having fimbriae with an average length of at least 0.4 μm for use in the treatment and/or prevention of infections or immune-related diseases.

21. A composition comprising one or more *L. casei* species having a whole genome G/C content of at least 47.5% and harbouring one or more catalase genes for use in the treatment and/or prevention of infections or immune-related diseases.

22. A composition comprising one or more *L. casei* species having a whole genome G/C content of at least 47.5%, harbouring one or more catalase genes and having fimbriae with an average length of at least 0.4 μm for use in the treatment and/or prevention of infections or immune-related diseases.

23 The *L. casei* species or composition for use according to any one of the embodiments 19 to 22 wherein said infections are oronasopharyngeal infections, in particular upper respiratory tract infections selected from the group comprising otitis media, pharyngitis, chronic sinusitis, acute sinusitis, rhinitis, flue, mucositis, caries, gingivitis, or halitosis and the like.

24. The *L. casei* species or composition for use according to anyone of the embodiments 19 to 22, wherein said infections are skin infections, in particular acne vulgaris, psoriasis, burn wounds, cellulitis, impetigo, athlete's feet (tinea pedis), fungal nail infections, or warts, and the like.

25. The *L. casei* species or composition for use according to anyone of the embodiments 19 to 22, wherein said infections are mastitis.

26. The *L. casei* species or composition for use according to anyone of the embodiments 19 to 22, wherein the infections are urogenital infections, in particular vaginal infections and bladder infections.

27. The *L. casei* species or composition for use according to anyone of the embodiments 19 to 22, wherein the infections are gastro-intestinal infections, in particular colitis, stomach infection, inflammatory bowel disease, irritable bowel syndrome and the like.

28. The *L. casei* species or composition for use according to anyone of the embodiments 19 to 22, wherein the immune-related diseases are selected from the group comprising hay fever, allergic rhinitis, allergic sinusitis, asthma, and the like.

29. Use of a *L. casei* species having a whole genome G/C content of at least 47.5% and harbouring one or more catalase genes as an adjuvant to promote an immune response during vaccination.

30. Use of a *L. casei* species having a whole genome G/C content of at least 47.5%, harbouring one or more catalase genes and having fimbriae with an average length of at least 0.4 µm as an adjuvant to promote an immune response during vaccination.

31. Use of a composition comprising one or more *L. casei* species having a whole genome G/C content of at least 47.5% and harbouring one or more catalase genes as an adjuvant to promote an immune response during vaccination.

32. Use of a composition comprising one or more *L. casei* species having a whole genome G/C content of at least 47.5%, harbouring one or more catalase genes as an adjuvant to promote an immune response during vaccination and having fimbriae with an average length of at least 0.4 µm as an adjuvant to promote an immune response during vaccination.

33. Use of a *L. casei* species having a whole genome G/C content of at least 47.5% and harbouring one or more catalase genes in personal hygiene industry, in particular in the production of tissues, protective masks or sprays.

34. Use of a *L. casei* species having a whole genome G/C content of at least 47.5%, harbouring one or more catalase genes and having fimbriae with an average length of at least 0.4 µm in personal hygiene industry, in particular in the production of tissues, protective masks or sprays.

35. Use of a composition comprising one or more *L. casei* species having a whole genome G/C content of at least 47.5%, and harbouring one or more catalase genes; in personal hygiene industry, in particular the production of tissues, protective masks or sprays.

36. Use of a composition comprising one or more *L. casei* species having a whole genome G/C content of at least 47.5%, harbouring one or more catalase genes, and having fimbriae with an average length of at least 0.4 µm; in personal hygiene industry, in particular the production of tissues, protective masks or sprays.

37. Use of a *L. casei* species having a whole genome G/C content of at least 47.5% and harbouring one or more catalase genes in cleaning industry, in particular in the production of a cleaning product.

38. Use of a *L. casei* species having a whole genome G/C content of at least 47.5%, harbouring one or more catalase genes, and having fimbriae with an average length of at least 0.4 µm in cleaning industry, in particular in the production of a cleaning product.

39. Use of a composition comprising one or more *L. casei* species having a whole genome G/C content of at least 47.5% and harbouring one or more catalase genes in cleaning industry, in particular in the production of a cleaning product.

40. Use of a composition comprising one or more *L. casei* species having a whole genome G/C content of at least 47.5%, harbouring one or more catalase genes, and having fimbriae with an average length of at least 0.4 µm in cleaning industry, in particular in the production of a cleaning product.

41. Use of a *L. casei* species having a whole genome G/C content of at least 47.5% and harbouring one or more catalase genes in air purification, in particular in air purification filters.

42. Use of a *L. casei* species having a whole genome G/C content of at least 47.5%, harbouring one or more catalase genes and having fimbriae with an average length of at least 0.4 µm in air purification, in particular in air purification filters.

43. Use of a composition comprising one or more *L. casei* species having a whole genome G/C content of at least 47.5% and harbouring one or more catalase genes in air purification, in particular in air purification filters.

44. Use of a composition comprising one or more *L. casei* species having a whole genome G/C content of at least 47.5%, harbouring one or more catalase genes and having fimbriae with an average length of at least 0.4 µm in air purification, in particular in air purification filters.

45. Use of a *L. casei* species having a whole genome G/C content of at least 47.5% and harbouring one or more catalase genes in the production of biomass.

46. Use of a *L. casei* species having a whole genome G/C content of at least 47.5%, harbouring one or more catalase genes and having fimbriae with an average length of at least 0.4 µm in the production of biomass.

47. Use of a composition comprising one or more *L. casei* species having a whole genome G/C content of at least 47.5% and harbouring one or more catalase genes in the production of biomass.

48. Use of a composition comprising one or more *L. casei* species having a whole genome G/C content of at least 47.5%, harbouring one or more catalase genes and having fimbriae with an average length of at least 0.4 µm in the production of biomass.

49. Use of a *L. casei* species according to anyone of embodiments 29, 30, 33, 34, 37, 38, 41, 42, 45 or 46, or use of a composition according to anyone of embodiments 31, 32, 35, 36, 39, 40, 43, 44, 47 or 48 wherein the one or more catalase genes are selected from the group comprising heme-catalase and manganese catalase.

50. Use of a *L. casei* species according to embodiments 29, 30, 33, 34, 37, 38, 41, 42, 45 or 46, or use of a composition according to anyone of embodiments 31, 32, 35, 36, 39, 40, 43, 44, 47 or 48, wherein said species has a genome with an average nucleotide identity to the genome sequence of the ATCC 393 *L. casei* strain of at least 93%.

51. Use of the isolated bacterial strain according to anyone of embodiments 1 to 5, or use of the composition according to embodiment 6 in the food industry.

52. Use of a *L. casei* species having a whole genome G/C content of at least 47.5% and harbouring one or more catalase genes in the food industry.

53. Use of a *L. casei* species having a whole genome G/C content of at least 47.5%, harbouring one or more catalase genes and having fimbriae with an average length of at least 0.4 µm in the food industry.

54. Use of a composition comprising one or more *L. casei* species having a whole genome G/C content of at least 47.5% and harbouring one or more catalase genes in the food industry.

55. Use of a composition comprising one or more *L. casei* species having a whole genome G/C content of at least 47.5%, harbouring one or more catalase genes and having fimbriae with an average length of at least 0.4 µm in the food industry.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

The present invention is based on the identification of a novel *L. casei* strain from the human upper respiratory tract, also indicated as the AMBR2 strain or *Lactobacillus* AMBR2. Said strain has been deposited with the Belgian Co-ordinated Collection of Micro-Organisms (BCCM) on Feb. 21, 2017 with accession number LMG P-30039.

Figure 3:
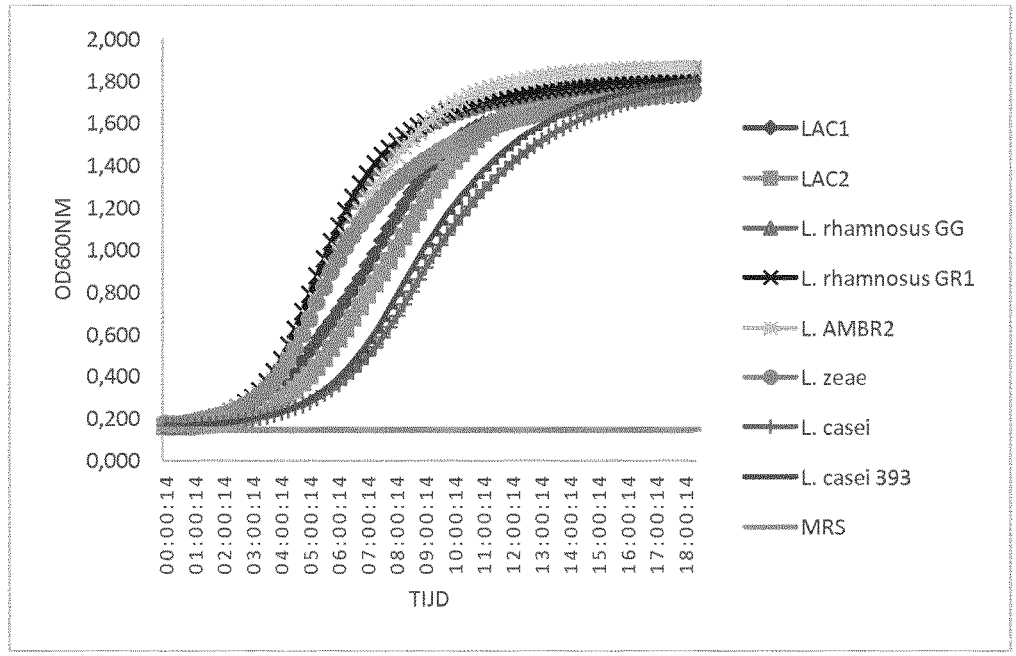
FIG. 3: Growth characteristics of different *Lactobacillus* species in MRS media.

Growth capacity of the novel isolated *L. casei* AMBR2 strain (LMG P-30039) was compared to the growth capacity of several other *Lactobacillus* strains as indicated in FIG. 3. Growth capacity of the novel isolated *L. casei* AMBR2 strain was found to be improved as compared to the growth capacity of other strains of the *Lactobacillus* species. In addition, the novel isolated strain is also characterized in that it comprises special fimbriae with an average length of at least 0.4 µm, thereby enhancing adhesion on epithelial cells.

Typical for this novel isolated strain is that it has a whole genome G/C content of 48.02%, which is higher than the expected whole genome G/C content in other *L. casei* strains. Further, said novel isolated bacterial strain *L. casei* with accession number LMG P-30039 harbours one or more catalases genes, in particular two catalase genes, wherein said catalase genes are selected from the group comprising heme-catalase and manganese catalase.

Figure 4:
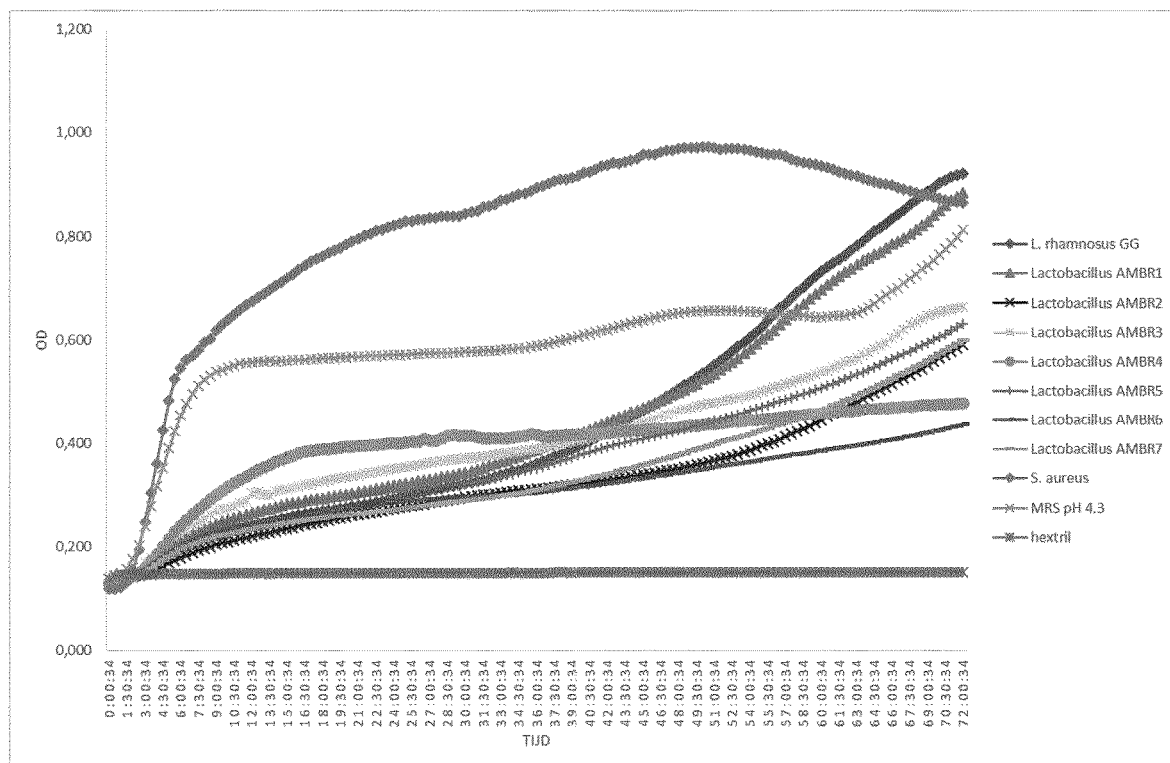
FIG. 4: Anti-pathogenic activity of different *Lactobacillus casei* strains against the growth of *Staphylococcus aureus*.
Figure 5:
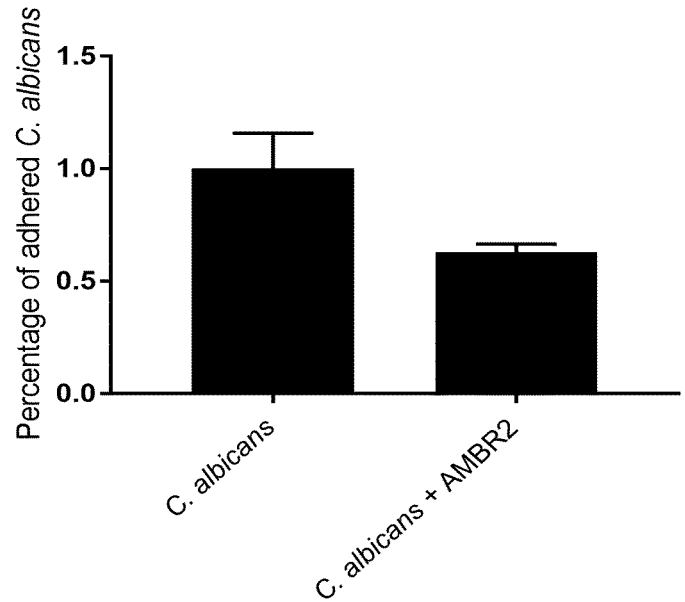
FIG. 5: Adhesion capacity *C. albicans* on vaginal epithelial cells in the presence of absence of the *L. casei* strain with accession number LMG P-30039.
Figure 6:
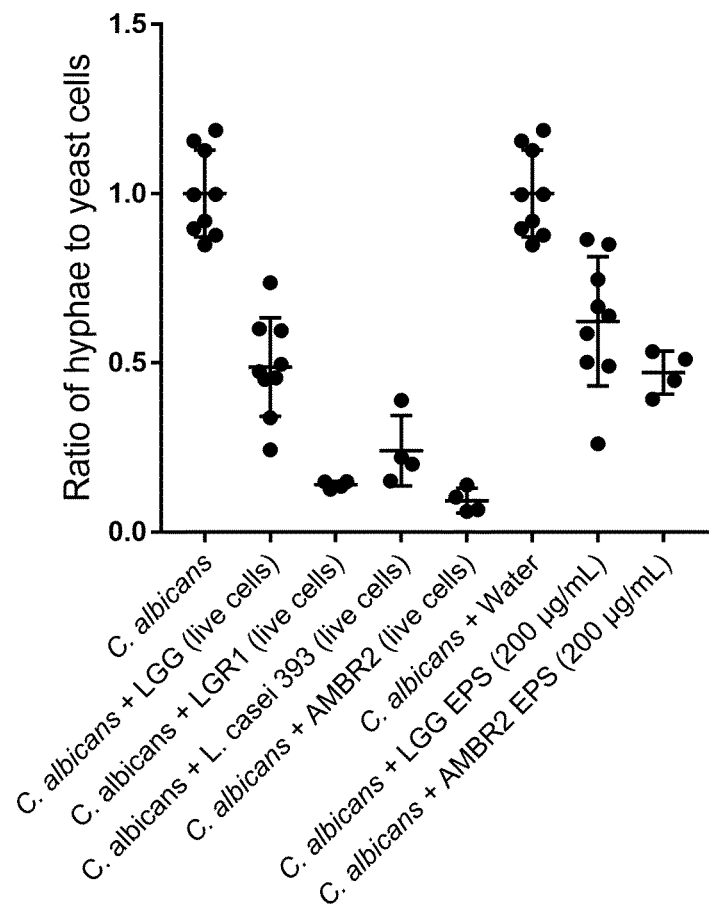
FIG. 6: Anti-Hyphae activity of *L. casei* LMG P-30039 (AMBR2).

Catalase is an important driver in establishing an oxidative stress resistant phenotype. Although lactic acid bacteria are generally defined as catalase negative, catalase activity has been found in members of the genera *Lactobacillus*, *Pediococcus*, and *Leuconostoc*. Also the novel isolated *L. casei* strain according to the present invention expresses a heme dependent catalase. Said heme dependent catalase shows more than 70% identity and more than 80% coverage with the *L. plantarum* WCSF1 heme dependent catalase (NCBI sequence YP_004891054), *L. sakei* heme dependent catalase (NCBI sequence WP_01137882) and *L. brevis* ATCC 367 catalase (NCBI sequence WP_011667631) on the protein level. In addition, also a gene encoding a manganese was identified in the novel strain according to the present invention. Said manganese shows more than 70% identity and more than 80% coverage with the *L. plantarum* ATCC 14431 Manganese catalase (RCSB Protein Databank accession number 1JKU) on the protein level. As a result, this novel isolated strain harbours a very oxidant resistant phenotype. Further, the novel isolated *L. casei* strain according to the present invention shows improved anti-pathogenic activity against *Staphylococcus aureus* (FIG. 4) and *Candida albicans* (FIG. 5-6). In addition, the novel *L. casei* AMBR2 strain also shows improved adhesion capacity to airway epithelial cells, vaginal epithelial cells and gut epithelial cells (FIG. 8-12).

Figure 13:
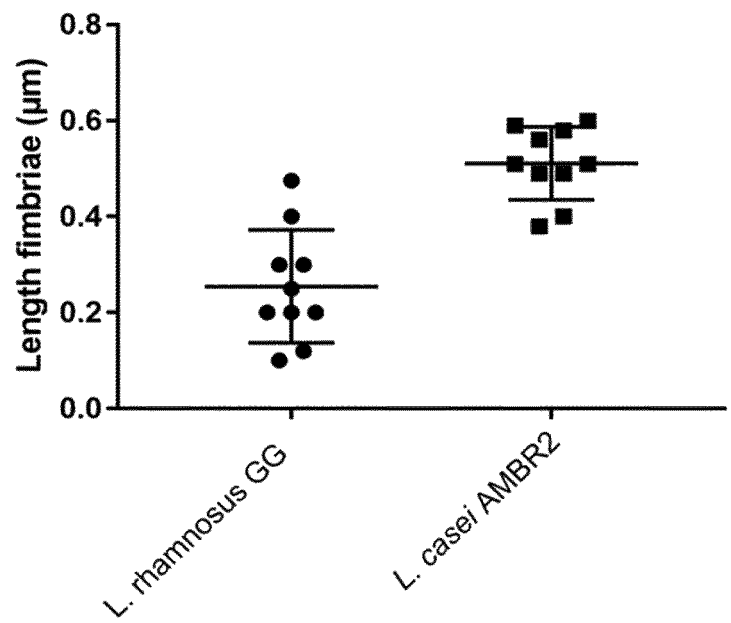
FIG. 13: Average length of the fimbriae of *L. rhamnosus* GG and the *L. casei* strain with accession number LMG P-30039 (AMBR2).

In addition, the novel isolated strain is also characterized in that it comprises special fimbriae with an average length of at least 0.4 µm; in particular special robust, glycosylated, serine-rich, single subunit fimbriae with an average length of at least 0.4 µm, thereby enhancing adhesion on epithelial cells (FIG. 13).

In a further embodiment, said novel *L. casei* strain may comprise special fimbriae with an average length of at least 0.4 µm. In another embodiment, said *L. casei* strain produces more exopolysacharides, in particular cell-wall polysaccharides, as compared to the reference *L. rhamnosus* GG. In an even further embodiment, the produced exopolysaccharides in the *L. casei* strain may be of a different form and/or with a different biological activity as compared to those produced by the *L. rhamnosus* GG.

In yet another embodiment, said novel *L. casei* strain prevents the epithelial barrier disruption, for example the epithelial barrier disruption induced by the super-toxin SEB of the *Staphylococcus*.

Based on these findings, the novel isolated bacterial AMBR2 strain deposited under accession number LMG P-30039 or a composition comprising said isolated bacterial AMBR2 strain is provided for use in the treatment and/or prevention of infections or immune-related diseases. Said infections are preferably oronasopharyngeal infections, skin infections, mastitis, urogenital infections or gastro-intestinal infections.

Oronasopharyngeal Infections are selected from infections of the oronasopharyngeal cavity or oral infections, preferably selected, but not limited, from the group comprising otitis media, pharyngitis, chronic sinusitis, acute sinusitis, rhinitis, flue, mucositis, caries, gingivitis, or halitosis, and the like. Skin infections are preferably selected from the group comprising acne vulgaris, psoriasis, burn wounds, cellulitis, impetigo, athlete's feet (tinea pedis), fungal nail infections, or warts, and the like. Urogenital infections are preferably selected from the group comprising vaginal infections or bladder infections. Gastro-intestinal infections are preferably selected from the group comprising colitis, stomach infection, inflammatory bowel disease, irritably bowel syndrome and the like.

As already indicated above, the isolated bacterial AMBR2 strain or composition comprising said strain according to the present invention is also provided for use in the treatment and/or prevention of immune-related diseases. Said immune-related diseases can be selected from the group comprising hay fever, allergic rhinitis, allergic sinusitis, asthma, and the like. In another embodiment, the present invention also provides the use of the isolated bacterial strain or a composition comprising said strain according to the present invention as an adjuvant to promote an immune response during vaccination.

Based on the finding that the novel isolated bacterial AMBR2 strain of the *L. casei* species with accession number LMG P-30039 shows improved adhesion capacity to respiratory epithelial cells and harbours a very oxidant resistant phenotype, the present invention also provides the use of said isolated bacterial strain or a composition comprising said bacterial strain in personal hygiene industry, in particular in the production of tissues, protective masks or sprays; even more in particular in the production of tissues, protective masks or sprays for the treatment and/or prevention of respiratory infections.

Based on its anti-microbial capacity, the use of the novel isolated bacterial AMBR2 strain or a composition comprising said strain according to the present invention is disclosed in cleaning industry, in particular in the production of a cleaning product. Said cleaning products are particularly intended for treatment and/or disinfection of surfaces.

In yet another embodiment, the use of the novel isolated bacterial AMBR2 strain or a composition comprising said strain according to the present invention is disclosed in air purification, in particular in air purification filters.

Further, and based on its capacity to produce lactic acid, the use of the novel isolated bacterial AMBR2 strain or a composition comprising said strain in the production of biomass is also disclosed. Said production of biomass can encompass, e.g. plant biomass, animal biomass and municipal waste biomass.

Further, the use of the novel isolated bacterial AMBR2 strain or a composition comprising said strain in the food industry is disclosed. Said food industry can encompass fermented food products (diary-based, worth soy) or the bioreactors and processing environments used in the food industry, whereby the AMBR2 strain or a composition comprising said strain can be used to decrease biofilm formation of unwanted or spoilage organisms. Thus, in a further embodiment, the use of the novel isolated bacterial AMBR2 strain or a composition comprising said strain in fermented food products such as diary-based, worth soy, is disclosed. In another embodiment, the use of the novel isolated bacterial AMBR2 strain or a composition comprising said strain in bioreactors and processing environments used in the food industry is disclosed.

Figure 17:
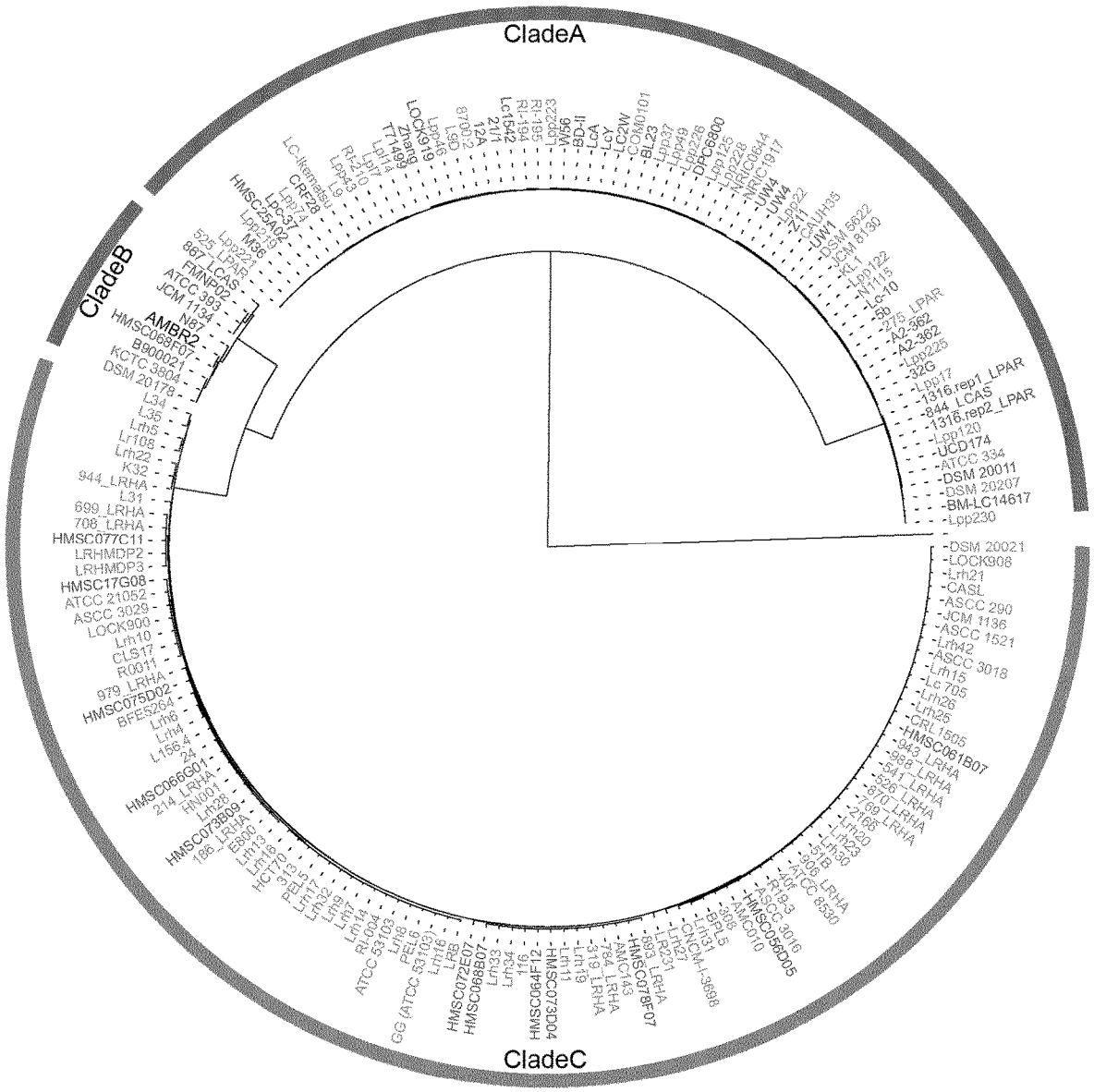
FIG. 17: Phylogenetic tree constructed of all 184 genome assemblies of the *L. casei* group.

In another aspect of the present invention, a novel group of *Lactobacillus casei* species was identified using different comparative genomic approaches. With this approach, 183 publically available *L. casei* group genome assemblies, comprising the species *L. paracasei, L. casei, L. rhamnosus* and *L. zeae*, together with one newly sequenced isolate from the human respiratory tract (the *L. casei* AMBR2 strain, deposited under accession number LMG P-30039) and three isolates from carrot juice fermentations were analysed (Example 2). With these approaches, three different taxonomic clades were identified based on a phylogenetic tree constructed on the alignment of 776 genes (FIG. 17), differences in whole genome G/C content (FIG. 18) and pairwise ANI-values (FIG. 19A)). One of these clades consists of only *L. casei* isolates (following the reclassification of *L. zeae* to *L. casei*, Salvetti et al. 2012), and each member is characterized by a high whole genome G/C content, in particular a whole genome G/C content of at least 47.5%, and by the presence of one or more catalase genes, wherein the catalase genes are selected from the group comprising heme-catalase and manganese. Further, each member of this clade is also characterized by an average nucleotide identity (ANI) value of at least 93% as compared to the genome sequence of the ATCC 393 *L. casei* strain.

Based on the identification of this novel clade, that also comprises the novel isolated *L. casei* AMBR2 strain (deposited under accession number LMG P-30039), the present invention further provides a *L. casei* species or a composition comprising one or more *L. casei* species for use in the treatment and/or prevention of infections and/or immune-related diseases, wherein said *L. casei* species has a whole genome G/C content of at least 47.5%, and harbours one or more, in particular two catalase genes. Said *L. casei* species may further comprise special fimbriae with an average length of at least 0.4 µm, in particular special robust, glycosylated, serine-rich, single-subunit fimbriae with an average length of at least 0.4 µm. In a further embodiment, the present invention provides said *L. casei* species having a whole genome G/C content of at least 47.5% and harbouring one or more catalase genes or a composition comprising one or more of said *L. casei* species for use in the treatment and/or prevention of oronasopharyngeal infections, in particular infections of the oronasopharyngeal cavity or oral infections, more in particular upper respiratory tract infections selected from the group comprising acute otitis media, pharyngitis, chronic sinusitis, acute sinusitis, rhinitis, flue, mucositis, caries, gingivitis, or halotosis and the like.

In a further embodiment, the present invention provides a *L. casei* species having a whole genome G/C content of at least 47.5% and harbouring one or more catalase genes or a composition comprising one or more of said *L. casei* species for use in the treatment and/or prevention of skin infections, in particular acne vulgaris, psoriasis, burn wounds, cellulitis, impetigo, athlete's feet (tinea pedis), fungal nail infections, or warts, and the like.

In still another embodiment, the present invention provides a *L. casei* species having a whole genome G/C content of at least 47.5% and harbouring one or more catalase genes or a composition comprising one or more of said *L. casei* species for use in the treatment and/or prevention of mastitis.

In yet another embodiment, the present invention provides a *L. casei* species having a whole genome G/C content of at least 47.5% and harbouring one or more catalase genes or a composition comprising one or more of said *L. casei* species for use in the treatment and/or prevention of urogenital infections, in particular vaginal infections and bladder infections.

In still a further embodiment, the present invention provides a *L. casei* species having a whole genome G/C content of at least 47.5% and harbouring one or more catalase genes or a composition comprising one or more of said *L. casei* species for use in the treatment and/or prevention of gastrointestinal infections, in particular colitis, stomach infection, inflammatory bowel disease, irritable bowel syndrome and the like. Said *L. casei* species may further comprise special fimbriae with an average length of at least 0.4 µm; in particular special robust, glycosylated, serine-rich, single-subunit fimbriae with an average length of at least 0.4 µm.

In another embodiment, the present invention provides a *L. casei* species having a whole genome G/C content of at least 47.5% and harbouring one or more catalase genes or a composition comprising one or more of said *L. casei* species for use in the treatment and/or prevention of immune-related diseases, in particular immune-related diseases selected from the group comprising hay fever, allergic rhinitis, allergic sinusitis, asthma, and the like. Said *L. casei* species may further comprise special fimbriae with an average length of at least 0.4 µm; in particular special robust, glycosylated, serine-rich, single-subunit fimbriae with an average length of at least 0.4 µm.

The present invention further discloses the use of a *L. casei* species having a whole genome G/C content of at least 47.5% and harbouring one or more catalase genes in personal hygiene industry. Also the use of a composition comprising one or more of said *L. casei* species in personal hygiene industry is disclosed. In particular, the use of *L. casei* species having a whole genome G/C content of at least 47.5% and harbouring one or more catalase genes or a composition comprising one or more of said *L. casei* species in the production of tissues, protective masks or sprays is disclosed. Even more in particular, said tissues, protective masks or sprays are directed towards the treatment and/or prevention of respiratory infections. Said *L. casei* species may further comprise special fimbriae with an average length of at least 0.4 µm; in particular special robust, glycosylated, serine-rich, single-subunit fimbriae with an average length of at least 0.4 µm.

In another aspect, the present invention discloses the use of a *L. casei* species or a composition comprising one or more of said *L. casei* species in air purification, in particular in air purification filters, wherein said *L. casei* species has a whole genome G/C content of at least 47.5% and harbours one or more catalase genes. Said *L. casei* species may further comprise special fimbriae with an average length of at least 0.4 µm; in particular special robust, glycosylated, serine-rich, single-subunit fimbriae with an average length of at least 0.4 µm.

In a further aspect, the present invention discloses the use of a *L. casei* species or a composition comprising one or more of said *L. casei* species in the production of biomass, wherein said *L. casei* species has a whole genome G/C content of at least 47.5% and harbours one or more catalase genes. Said *L. casei* species may further comprise special fimbriae with an average length of at least 0.4 µm; in particular special robust, glycosylated, serine-rich, single-protein subunit fimbriae with an average length of at least 0.4 µm.

Further, the use of a *L. casei* species or a composition comprising one or more of said *L. casei* species in the food industry is disclosed, wherein said *L. casei* species has a whole genome G/C content of at least 47.5% and harbours one or more catalase genes. Said *L. casei* species may further comprise special fimbriae with an average length of at least 0.4 µm; in particular special robust, glycosylated, serine-rich, single-protein subunit fimbriae with an average length of at least 0.4 µm. Said food industry can encompass fermented food products (diary-based, worth soy) or the bioreactors and processing environments used in the food industry, whereby the *L. casei* species or a composition comprising said strain can be used to decrease biofilm formation of unwanted or spoilage organisms. Thus, in a further embodiment, the use of said *L. casei* species or a composition comprising one or more of said *L. casei* species in fermented food products such as diary-based, worth soy, is disclosed. In another embodiment, the use of said *L. casei* species or a composition comprising one or more of said *L. casei* species in bioreactors and processing environments used in the food industry is disclosed.

Further referring to the different uses of the *L. casei* species according to the present invention or the composition comprising one or more of said *L. casei* species according to the present invention, said *L. casei* species harbours one or more catalase genes, wherein the one or more catalase genes are selected from the group comprising heme-catalase and manganese catalase.

In yet another embodiment of the present invention, and also referring to the different uses of the *L. casei* species or composition comprising said *L. casei* species according to the present invention, said species has a genome with an average nucleotide identity to the genome sequence of the ATCC 393 *L. casei* strain of at least 93%.

In the context of the present invention, the term "average length of the fimbriae" is meant to be be based on analysis through scanning electron microscopy (SEM) after three times washing of the bacteria with a suitable buffer (e.g. Phosphate Buffered Saline), with in-between centrifugation of the cells at min. 6000 g. The length of at least 10 fimbriae on one or two bacterial cells is carefully determined (expressed in µm) and the average is determined.

EXAMPLES

Example 1: Isolation of the Novel *L. casei* Strain (Deposited Under Accession Number LMG P-30039) and Microbiome Comparison Between the Nose (N) and Nasopharynx (NF) of Healthy Subjects (CON) and Patients with Chronic Rhinosinusitis (CRS) for the Presence or Absence of Lactobacilli in their Microbiome Profiles Materials and Methods Samples were collected in the framework of the Clinical trial NCT 02 933983 (https://clinicaltrials.gov/ct2/show/NCT02933983). The method for DNA extraction and 16 S amplicon sequencing was recently published in De Boeck et al., *Frontiers in Microbiology* 2017.

Results

Figure 1:
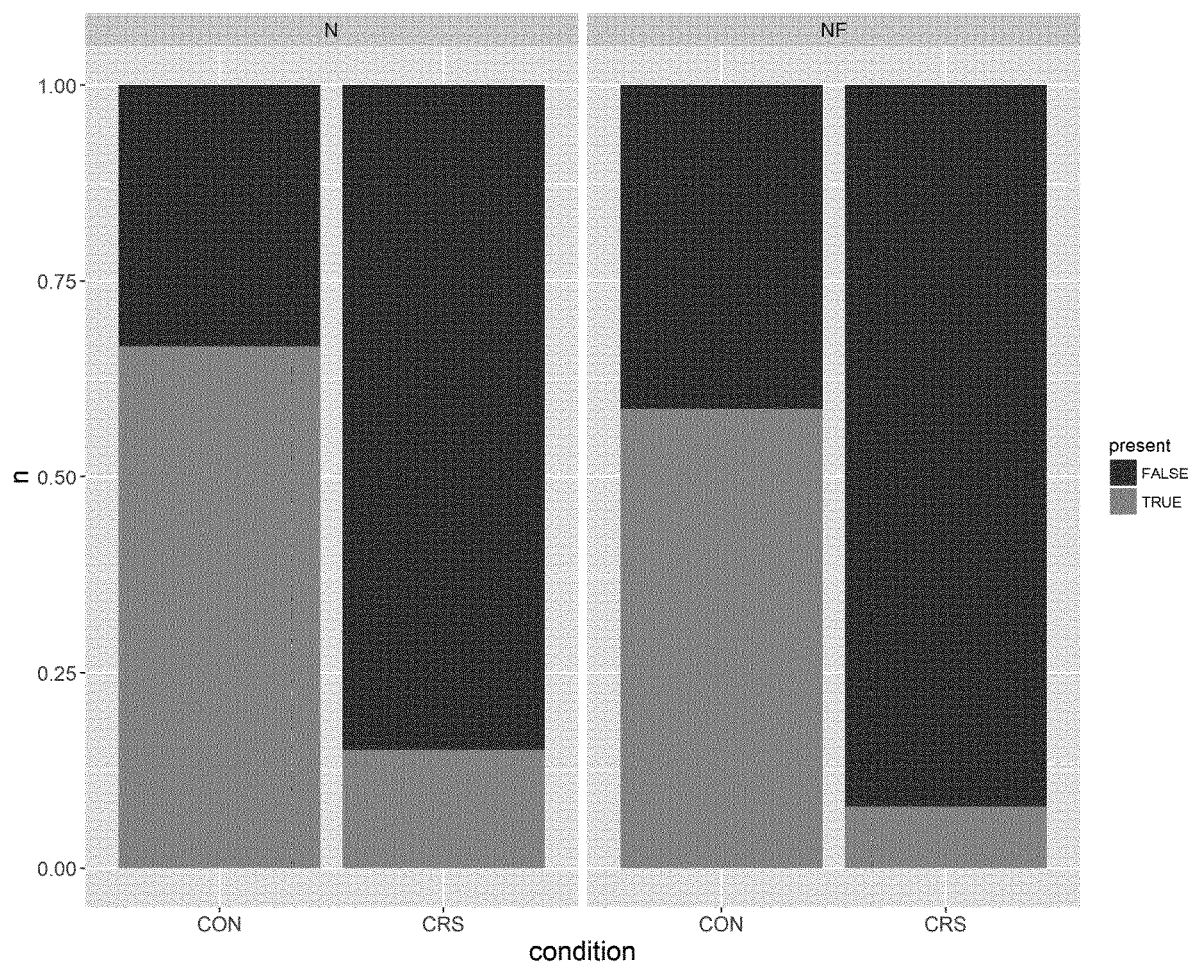
FIG. 1 Microbiome comparison between the nose (N) and nasopharynx (NF) of healthy subjects (CON) and patients with chronic rhinosinusitis (CRS) for the presence (TRUE) or absence (FALSE) of lactobacilli in their microbiome profile.
Figure 2:
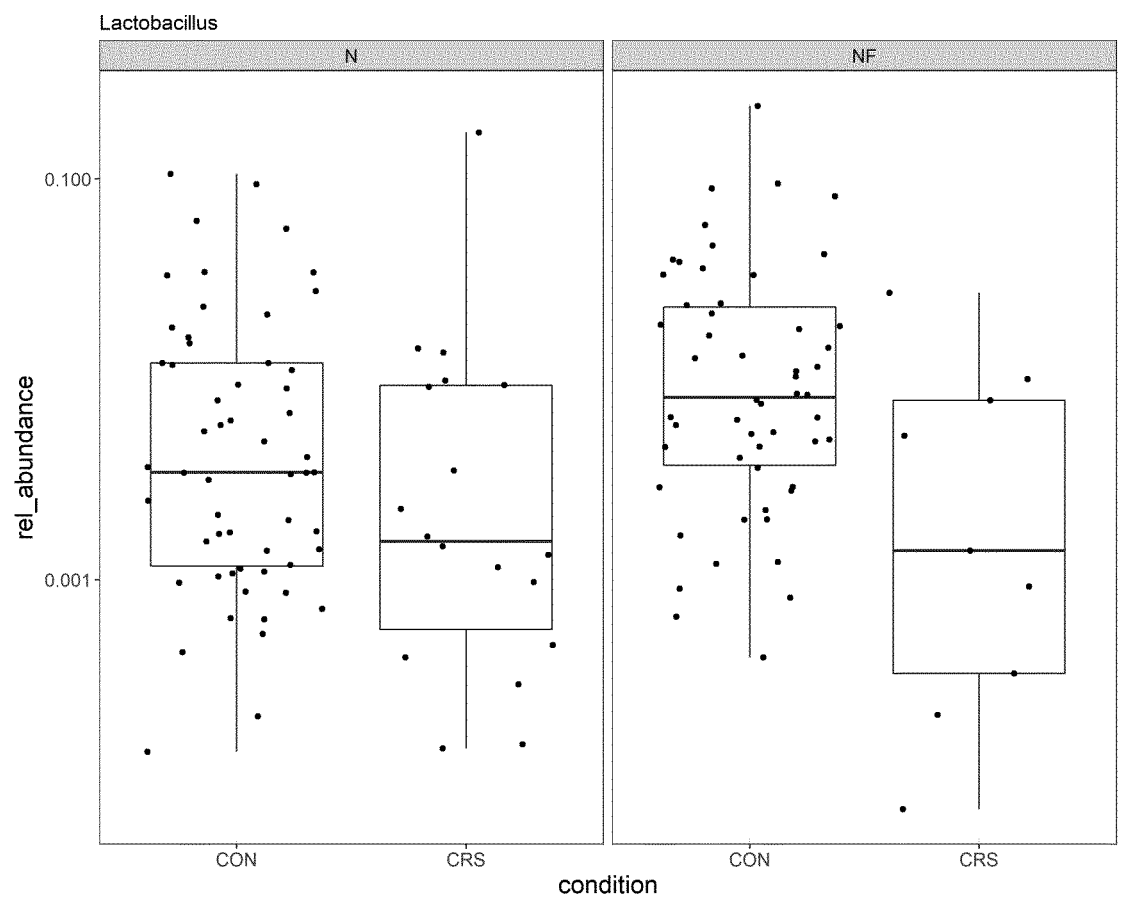
FIG. 2: Comparison of the relative abundance of lactobacilli in the nose (N) and nasopharynx (NF) of healthy subjects (CON) and patients with chronic rhinosinusitis (CRS) in case lactobacilli are present in the profile.

At least 66% of the healthy subjects (CON) contains lactobacilli in the nose (N) and 59% in the nasopharynx (NF), while this is drastically reduced to less than 15% and less than 10% for the chronic rhinosinusitis (CRS) patients for nose and nasopharynx respectively (FIG. 1). Comparison of the relative abundance of lactobacilli in the nose and nasopharynx of healthy subjects and patients with chronic rhinosinusitis when lactobacilli are present in the profile shows that lactobacilli are not only more present in healthy controls, but also have higher relative abundances in healthy subjects compared to CRS patients (FIG. 2).

Example 2: Characterization of the Novel Isolated L. casei Strain (Deposited Under Accession Number LMG P-30039)

Material and Methods

Bacterial growth assays. Overnight cultures of the lactobacilli ($\pm 2 \times 10^9$ CFU/ml) were added to the wells of a microtiterplate in a 100-fold dilution. *Lactobacillus* cultures were allowed to grow in MRS medium (Difco, Belgium) for 18 h and the optical density was measured every 15 min at 600 nm using a Synergy HTX multi-mode reader (Biotek, Drogenbos, Belgium).

Time-course analysis of the antimicrobial activity of *Lactobacillus* supernatant for *S. aureus* growth in suspension. For the time-course analysis, an overnight culture of *S. aureus* ($\pm 4 \times 10^9$ CFU/ml) was added to the wells of a microtiterplate in a 100-fold dilution, supplemented with 10% *Lactobacillus* supernatant. Hexetidine (0.1%) and MRS medium at pH3.6 were used as positive controls. *S. aureus* cultures were allowed to grow for 72 h and the optical density was measured every 30 min at 600 nm using a Synergy HTX multi-mode reader (Biotek, Drogenbos, Belgium). Each condition was measured at least in triplicate and the average OD was calculated.

Inhibition of *C. albicans* adherence to epithelial cells by *Lactobacillus* species. The influence of lactobacilli on the adherence of *Candida* species to vaginal epithelial VK2/E6E7 cells was investigated by adding a volume of 1 ml containing *Candida* cells ($10^6$ CFU) and lactobacilli ($10^8$ CFU) simultaneously to tissue culture plate wells containing confluent monolayers of epithelial cells, which were allowed to incubate at 37° C. for 1 h to mediate adherence. After incubation, the cells were washed three times with Dulbecco's PBS to remove all non-adhered cells and the number of adhered *Candida* cells to the VK2/E6E7 cells was determined by the macrodilution method on Sabouraud agar (Carl Roth), which is selective for fungal species. Each condition was carried out at least in triplicate.

Isolation of EPS. The EPS of the *Lactobacillus* strains were isolated with the extraction protocol described previously (Lebeer et al., 2007). Briefly, the lactobacilli were grown to an optical density of 0.6 and washed with phosphate-buffered saline. EPS was then extracted by incubation in 0.05 M EDTA (Sigma Aldrich, Diegem, Belgium) (shaking, on ice), followed by ethanol precipitation and dialysis against distilled water (Spectra/Por® dialysis membrane [Spectrum Laboratories, Breda, The Netherlands]). Afterwards, samples were treated with trichloroacetic acid (Sigma Aldrich) to remove proteins, dialyzed against water and filter sterilized (pore size 0.2 µm [VWR, Haasrode, Belgium]). The total amount of carbohydrate was estimated by the phenol-sulfuric acid method (DuBois et al., 1956). Samples were freeze-dried in a FreeZone 1 Liter Benchtop Freeze Dry System (Model 7740030) (Labconco, Mo., USA) and stored at 4° C. until use. Before use, the EPS were dissolved in pure water. Cytokine production in THP-1 macrophages was monitored by quantitative RT-PCR as described in (Vargas Garcia et al., 2015; AEM)

Inhibition of hyphal formation by *C. albicans*. *C. albicans* hyphae ($10^6$ CFU/ml) were induced by fetal bovine serum, while incubated with or without lactobacilli ($10^8$ CFU/ml). After incubation, at least one hundred yeast cells and/or hyphae in at least three biological repeats were counted and the ratio of hyphae to yeast cells was calculated.

Adhesion to epithelial cells. The adherence capacity of the *Lactobacillus* isolates to vaginal epithelial VK2/E6E7 cells, intestinal epithelial Caco-2 cells and airway epithelial Calu-3 cells was investigated by adding the lactobacilli ($10^8$ CFU/ml) to epithelial monolayers. After one of incubation to mediate adherence, the cells were washed three times with Dulbecco's PBS to remove all non-adhered cells and the remaining cells were loosened and quantified by the macrodilution method on MRS agar.

Expression of special fimbriae. The presence of pili or fimbriae (hear-like surface appendages) in the *L. casei* LMG P-30039 (AMBR2) strain and the reference probiotic strain *L. rhamnosus* GG was evaluated using scanning electron microscopy (SEM). Bacteria were spotted on a gold-coated membrane and fixed with 2.5% glutaraldehyde (in 0.1M Na-cacodylate) for 1 hour at room temperature (RT), followed by a further overnight fixation at 4° C. Bacteria were then rinsed 3 times for 20 min. and left overnight in cacodylate buffer (containing 7.5% saccharose) at 4° C. Subsequently, bacteria were dehydrated in an ascending series of ethanol (50%, 70%, 90%, 95%), each for 30 min at RT, and 3×30 min. in 100% ethanol, and critical point dried in a Leica EM Ace 600 coater. The membranes were mounted on a stub and coated with 5 nM of carbon in a Leica EM Ace 600 coater. SEM-imaging was performed with a Quanta FEG250 SEM system (Thermo Fischer, Asse, Belgium).

Enhancement of epithelial barrier integrity. The effect of *L. casei* LMG P-30039 (AMBR2) on the restoration of the nasal epithelial barrier was determined as described in Steelant et al. (2018; Journal of Allergy & Clinical Immunology). Male BALB/c (6-8 weeks) were obtained from Harlan (Horst, The Netherlands) and were kept under conventional conditions. M4 Nice were 3 times endonasally instilled with SEB (10 µg/ml) µl), or saline at 1-hour intervals. One hour after the last endonasal instillation, 20 µL fluorescein isothiocyanate-dextran 4 kDa (FD4) (50 mg/mL) was applied endonasally allowing evaluation of nasal mucosal permeability. One hour later, serum and nasal mucosa were collected for further analysis.

Results

Growth capacity of the novel isolated *L. casei* AMBR2 strain (LMG P-30039) was compared to the growth capacity of several other *Lactobacillus* strains as indicated in FIG. 3. Growth capacity of the novel isolated *L. casei* AMBR2 strain was found to be improved as compared to the growth capacity of other strains of the *Lactobacillus* species.

Figure 7:
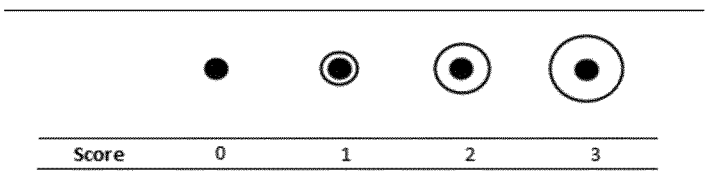
FIG. 7: Antimicrobial and antibiofilm activity of the *L. casei* strain with accession number LMG P-30039 (AMBR2).

Further, the novel isolated *L. casei* strain according to the present invention shows improved anti-pathogenic activity against *Staphylococcus aureus* (FIG. 4) and *Candida albicans* (FIG. 5-6). Further, the *L. casei* AMBR2 strain show excellent antimicrobial activities against respiratory pathogens such as *Moraxella catarrhalis, Haemophilus influenzae, Staphylococcus aureus, Shigella flexneri, Shigella sonnei, Escherichia coli* and *Candida albicans*. In addition, its supernatant shows unique antibiofilm activity against *Stenotrophomonas maltophila* (FIG. 7).

In addition, the novel *L. casei* AMBR2 strain also shows improved adhesion capacity to airway epithelial cells, vaginal epithelial cells and gut epithelial cells (FIG. 8-12).

The novel isolated *L. casei* strain further shows expression of fimbriae or pili which are on average clearly longer as compared to the fimbriae that are expressed on the reference *Lactobacillus rhamnosus* GG strain (Table 1 and FIG. 13).

TABLE 1 comparing fimbriae properties based on SEM

| SEM analysis | *L. rhamnosus* GG | *L. casei* LMG P-30039 (AMBR2) |
|---|---|---|
| Number of fimbriae on (piliated) cells | 14 | 6.25 |
| Length of fimbriae | Very variable: between 0.1 µm and 1 µm, on average 0.25 µm | on average 0.5 µm, more robust, less variation in length |
| "Stretch" | Rather "limp" | Completely stretched |
| "Substrate" | Other LGG cells | The membrane |
| Presence after spray-drying | Removed | Still present |

Figure 14:
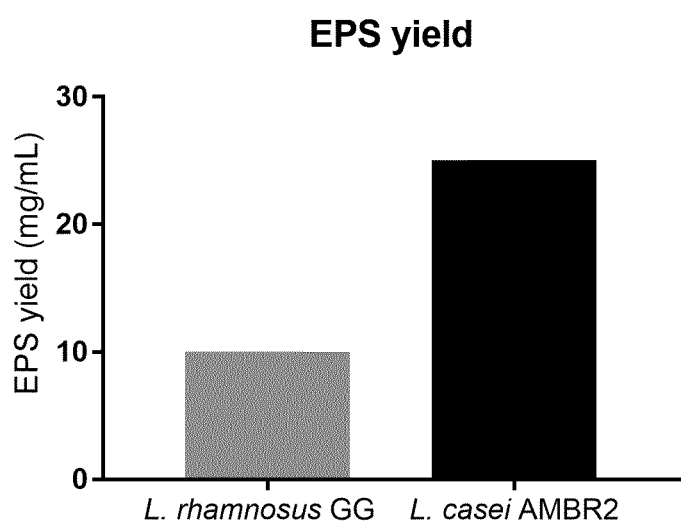
FIG. 14: Comparison between cell wall polysaccharide (CW-PS) yield form *L. rhamnosus* GG and *L. casei* strain with accession number LMG P-30039 (AMBR2)
Figure 15A:
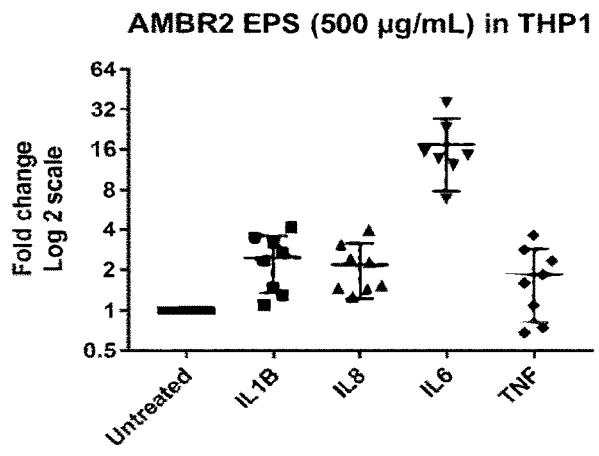
FIG. 15A: Effect of CW-PS from the *L. casei* strain with accession number LMG P-30039 (AMBR2) on the cytokine response in THP1 macrophages.
Figure 15B:
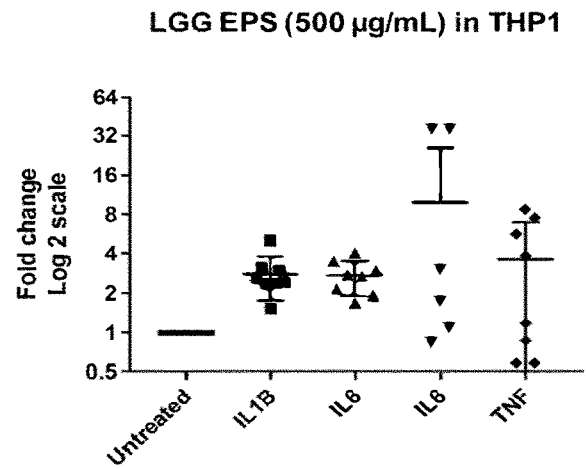
FIG. 15B: Effect of CW-PS from the *L. casei* strain with the *L. rhamnosus* GG on the cytokine response in THP1 macrophages.

Further, the novel *L. casei* LMG P-30039 (AMBR2) strain produces more exopolysaccharide, which is also of a different form and with different biological activity as compared to the *L. rhamnosus* GG and any other *Lactobacillus*. Extraction of the cell-wall EPS (CW-PS) of *L. casei* AMBR2 yields approximately 25 mg/ml, which is more than twice the yield of CW-PS form *L. rhamnosus* GG (FIG. 14).

Our data further show that CW-PS from *L. casei* LMG P-30039 (AMBR2) can modulate the cytokine response in THP1 macrophages. After cell differentiation with phorbol myristate acetate, the THP1 macrophages were stimulated with 500 µg/ml CW-PS from *L. casei* AMBR2 and *L. rhamnosus* GG. Based on qPCR, we observed a similar cytokine induction for both types of EPS, although IL-6 seems to be more induced by the *L. casei* AMBR2 strain.

Figure 16:
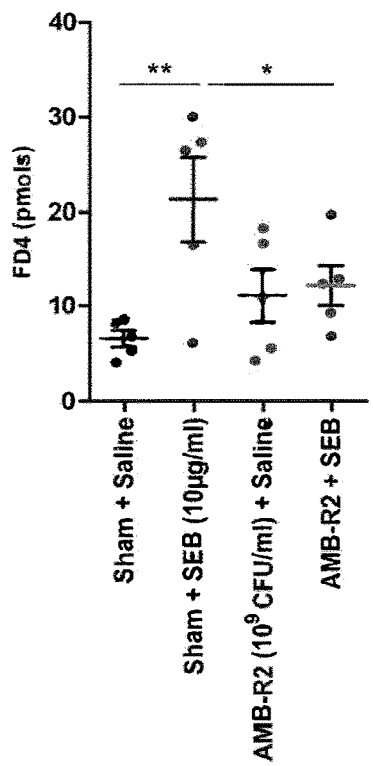
FIG. 16: Epithelial barrier disruption induced by the super-toxin SEB of *Staphylococcus* and counteraction by *L. casei* LMG P-30039 (AMBR2).

Finally, the *L. casei* AMBR2 strain prevents disruption of the epithelial barrier disruption induced by the super-toxin SEB of *Staphylococcus* (FIG. 16).

Example 2: Characterization of a Novel Group of *L. casei* Species Members

Material and Methods

Sequencing of Bacterial Isolates and NCBI Genomic Assemblies

Whole-genome sequencing was performed using the Nextera XT DNA Sample Preparation kit (Illumina), and sequenced by means of the Illumina MiSeq platform using 2×250 cycles at the Center of Medical Genetics Antwerp (University of Antwerp). Assembly was performed using SPAdes 3.8.0 (Bankevich et al., 2012). All genomic assemblies classified as *L. casei, L. paracasei, L. rhamnosus* and *L. zeae* (210 in total) were downloaded from NCBI on 19 Feb. 2017, using in-house scripts. In addition, all unclassified *Lactobacillus* assemblies (annotated as *Lactobacillus* sp.; 28 in total) were screened for *L. casei* group members by blasting (Camacho et al., 2009) them against a filtered RDP database (v11) (Cole et al., 2014) which contained only good quality *Lactobacillus* 16S rRNA sequences longer than 1200 nt from cultured isolates. This resulted in 15 additional assemblies which were subjected to quality control.

Quality Control and Annotation

The quality of the genomic assemblies was evaluated using the output generated by Quast 4.3 (Gurevich et al., 2013). After visualization of different quality control parameters, genomes with a N75<10.000 bp and a number of N's per 100.000 bases higher than 500 were discarded. Subsequently, one genomic assembly (GCA_001063295) was removed as it had a genome size of 5.8 Mbp and was identified as a hybrid assembly. Next, a custom Genus specific BLAST database was created using all complete *Lactobacillus* genomes found on NCBI. This database was used in Prokka (Seemann, 2014) with the --usegenus option, to annotate all genomic assemblies.

Construction of Phylogenetic Tree

Generation of the gene sets used as input for construction of the phylogenetic tree was done using Roary (Page et al., 2015) with a minimum blastp percentage identity of 70 and a threshold of 96 as percentage of isolates a gene must be in to be defined as a core gene. These core genes were translated and compared with a BLAST database of the outgroup GCA_000026065 (*L. sakei*) genome proteins. All hits with a coverage >75% and percentage identity >50% were added to the alignment using in house scripts. This alignment was used in RaxML 8.2.9 (Stamatakis, 2014) to build a maximum likelihood phylogenetic tree with the --a option which combines a rapid bootstrap algorithm with an extensive search of the tree space starting from multiple different starting trees. The main tree was plotted in iTOL (Letunic and Bork, 2016), while the subtrees were made using the R (R Core Team, 2015) package ggtree (Yu et al., 2016).

GC-Content

The whole genome GC-content and the GC-content per gene was calculated using Quast 4.3 (Gurevich et al., 2013) and infoseq from the EMBOSS 6.6.0.0 (Rice et al., 2000), respectively. Visualization was done in R using ggplot2 (Wickham, 2009).

ANIb, ANIm and TETRA

All pairwise ANIb, ANIm and TETRA values were calculated using the Python pyani-package and visualized using ggtree (Yu et al., 2016).

Interest Driven Approaches

For all interest driven approaches three different methods were used. First, the presence of the genes of interest, such as catalase gene, was evaluated based on their annotation. Secondly, the literature was screened manually for known variants of the genes of interest. These genes were then blasted against the representative core genes of each clade and the hits were evaluated. Finally, as a third approach, if possible, the PFAM database was used to download HMMs of the protein families of the gene of interest. Hmmer (Finn et al., 2011) was then used to scan the representative core genes of each clade against these HMMs.

Results

Table 2 gives an overview of all public available genomes (NCBI; 19 Feb. 2017) belonging to the *L. casei* group that were used in this study. In total, 183 public genome assemblies passed QC (N75 value <10.000 bp and a number of N's per 100.000 bases lower than 500). Of these genomes, 92 were classified as *L. rhamnosus*, 36 as *L. casei*, 38 as *L. paracasei* and 2 as *L. zeae*. In addition to the public genomes classified as *L. casei* group, we screened all unclassified *Lactobacillus* genomes (categorize as *Lactobacillus* sp. on NCBI) for *L. casei* group members by comparing their 16S rDNA sequences to a filtered version of the RDP database (v11) (Cole et al., 2014). This resulted in an additional 15 genomes. Furthermore, one newly sequenced *Lactobacillus casei* strain (AMBR2), isolated from the human URT, was added to the analysis. This led to a total of 184 studied *L. casei* group strains.

Taxonomic Structure

GC Content

Figure 18:
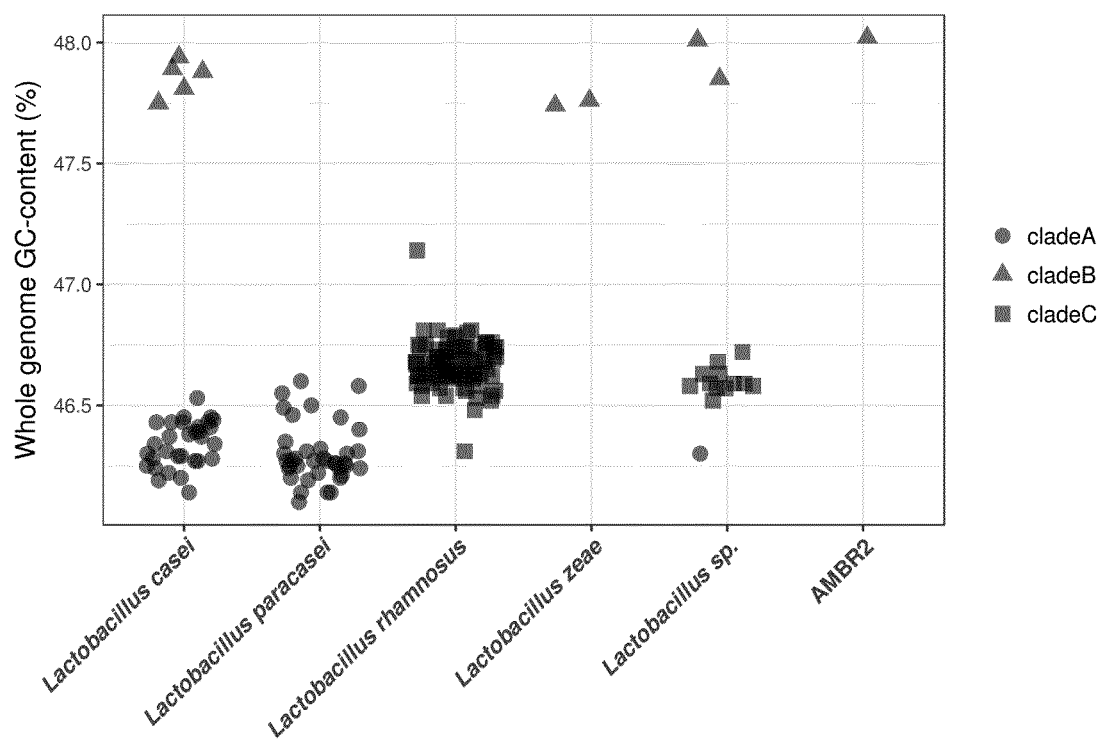
FIG. 18: Whole genome G/C content of the studied genome assemblies.
Figure 19A:
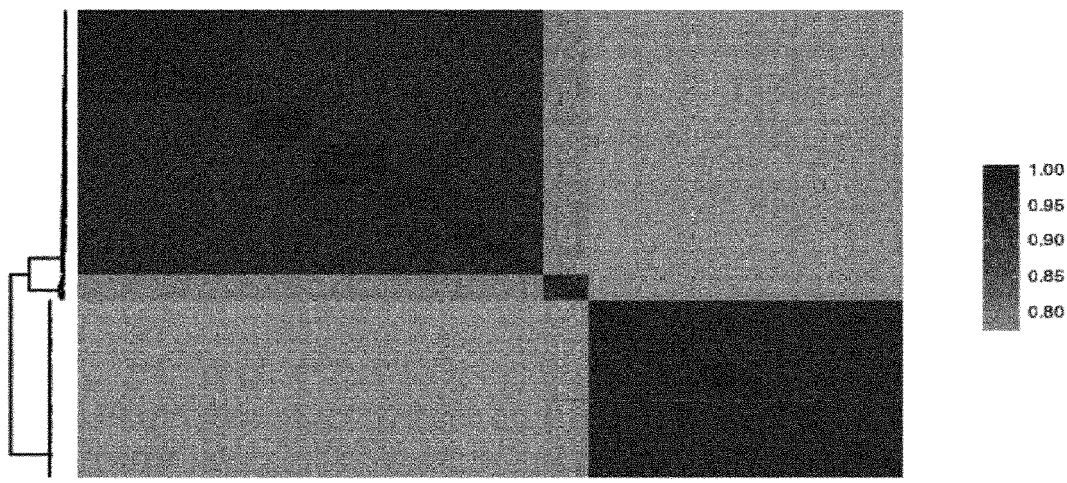
FIG. 19A: Pairwise ANIb values for all studied genomes.
Figure 19B:
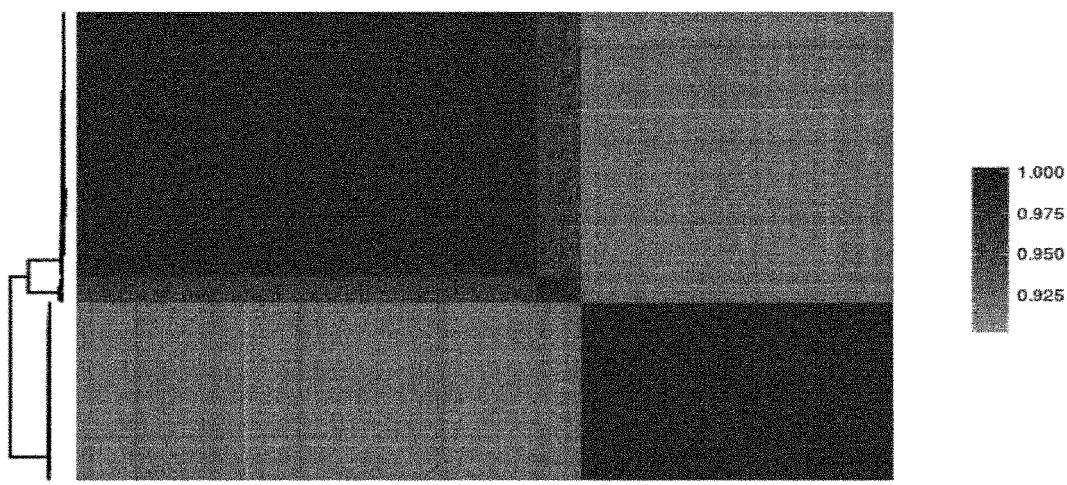
FIG. 19B: Pairwise TETRA values for all studied genomes.

The GC content of all assemblies is shown in FIG. 18. This figure shows that the GC-content of the *L. paracasei, L. rhamnosus*, and *L. zeae* species is stable within one species with respective average values of 46.3, 46.7 and 47.8. Overlap between these species is small or nonexistent.

In contrast, *L. casei* genomes can be divided into two groups. A large group showing a GC content value in the range of that of *L. paracasei*, while five genomes show a much higher GC content, similar to that of the *L. zeae* genomes. As for the unclassified assemblies (categorized as *Lactobacillus* sp.), two genomes show a GC-content as high as the *L. zeae* genomes, while the rest of them are within the *L. rhamnosus/L. paracasei* range. The genome sequence of our new isolate, which we designated as *L. casei* AMBR2, shows a GC content similar to other *L. zeae* genomes.

TABLE 2

An overview of all publicly available genomes belonging to the *L. casei* group that were used in this study. If available, the strain name is given in the second column.

| *Lactobacillus* species | strain | accession number | clade |
|---|---|---|---|
| *Lactobacillus casei* | Zhang | GCA_000019245 | cladeA |
| *Lactobacillus casei* | BL23 | GCA_000026485 | cladeA |
| *Lactobacillus casei* | BD-II | GCA_000194765 | cladeA |
| *Lactobacillus casei* | LC2W | GCA_000194785 | cladeA |
| *Lactobacillus casei* | 12A | GCA_000309565 | cladeA |
| *Lactobacillus casei* | 42756 | GCA_000309585 | cladeA |
| *Lactobacillus casei* | 32G | GCA_000309605 | cladeA |
| *Lactobacillus casei* | A2-362 | GCA_000309625 | cladeA |
| *Lactobacillus casei* | CRF28 | GCA_000309645 | cladeA |
| *Lactobacillus casei* | M36 | GCA_000309665 | cladeA |
| *Lactobacillus casei* | T71499 | GCA_000309685 | cladeA |
| *Lactobacillus casei* | UCD174 | GCA_000309705 | cladeA |
| *Lactobacillus casei* | UW1 | GCA_000309725 | cladeA |
| *Lactobacillus casei* | UW4 | GCA_000309745 | cladeA |
| *Lactobacillus casei* | Lc-10 | GCA_000309765 | cladeA |
| *Lactobacillus casei* | Lpc-37 | GCA_000309785 | cladeA |
| *Lactobacillus casei* | W56 | GCA_000318035 | cladeA |
| *Lactobacillus casei* | UW4 | GCA_000376145 | cladeA |
| *Lactobacillus casei* | LcY | GCA_000388095 | cladeA |
| *Lactobacillus casei* | LcA | GCA_000400585 | cladeA |
| *Lactobacillus casei* | LOCK919 | GCA_000418515 | cladeA |
| *Lactobacillus casei* | 5b | GCA_000474615 | cladeA |
| *Lactobacillus casei* | A2-362 | GCA_000510825 | cladeA |
| *Lactobacillus casei* | JCM 1134 | GCA_000615205 | cladeB |
| *Lactobacillus casei* | ATCC 393 | GCA_000829055 | cladeB |
| *Lactobacillus casei* | N87 | GCA_001013375 | cladeB |
| *Lactobacillus casei* | 1316.rep1_LPAR | GCA_001062665 | cladeA |
| *Lactobacillus casei* | 1316.rep2_LPAR | GCA_001062695 | cladeA |
| *Lactobacillus casei* | 844_LCAS | GCA_001066565 | cladeA |
| *Lactobacillus casei* | 867_LCAS | GCA_001066695 | cladeB |
| *Lactobacillus casei* | DSM 20011 | GCA_001433735 | cladeA |
| *Lactobacillus casei* | DPC6800 | GCA_001469115 | cladeA |
| *Lactobacillus casei* | Lc1542 | GCA_001540885 | cladeA |
| *Lactobacillus casei* | BM-LC14617 | GCA_001636215 | cladeA |
| *Lactobacillus casei* | Z11 | GCA_001885295 | cladeA |
| *Lactobacillus casei* | B900021 | GCA_001940585 | cladeB |
| *Lactobacillus paracasei* | ATCC 334 | GCA_000014525 | cladeA |
| *Lactobacillus paracasei* | 362, 5013889 | GCA_000155515 | cladeA |
| *Lactobacillus paracasei* | Lpp230 | GCA_000409815 | cladeA |
| *Lactobacillus paracasei* | Lpl7 | GCA_000409835 | cladeA |
| *Lactobacillus paracasei* | Lpp122 | GCA_000409855 | cladeA |
| *Lactobacillus paracasei* | Lpp46 | GCA_000409875 | cladeA |
| *Lactobacillus paracasei* | Lpp226 | GCA_000409895 | cladeA |
| *Lactobacillus paracasei* | Lpp120 | GCA_000409935 | cladeA |
| *Lactobacillus paracasei* | Lpp223 | GCA_000409955 | cladeA |
| *Lactobacillus paracasei* | Lpp228 | GCA_000409995 | cladeA |
| *Lactobacillus paracasei* | Lpp221 | GCA_000410015 | cladeA |
| *Lactobacillus paracasei* | Lpp49 | GCA_000410035 | cladeA |
| *Lactobacillus paracasei* | Lpp17 | GCA_000410135 | cladeA |
| *Lactobacillus paracasei* | Lpp22 | GCA_000410155 | cladeA |
| *Lactobacillus paracasei* | Lpp225 | GCA_000410175 | cladeA |
| *Lactobacillus paracasei* | Lpp219 | GCA_000410195 | cladeA |
| *Lactobacillus paracasei* | Lpp74 | GCA_000410235 | cladeA |
| *Lactobacillus paracasei* | Lpl14 | GCA_000410335 | cladeA |
| *Lactobacillus paracasei* | Lpp37 | GCA_000410415 | cladeA |
| *Lactobacillus paracasei* | Lpp43 | GCA_000410455 | cladeA |
| *Lactobacillus paracasei* | Lpp125 | GCA_000410475 | cladeA |
| *Lactobacillus paracasei* | COM0101 | GCA_000508845 | cladeA |
| *Lactobacillus paracasei* | N1115 | GCA_000582665 | cladeA |
| *Lactobacillus paracasei* | JCM 8130 | GCA_000829035 | cladeA |
| *Lactobacillus paracasei* | DSM 20207 | GCA_000949485 | cladeA |
| *Lactobacillus paracasei* | NRIC1917 | GCA_000958505 | cladeA |
| *Lactobacillus paracasei* | NRIC0644 | GCA_000958525 | cladeA |
| *Lactobacillus paracasei* | 275_LPAR | GCA_001076595 | cladeA |
| *Lactobacillus paracasei* | 525_LPAR | GCA_001076935 | cladeA |
| *Lactobacillus paracasei* | CAUH35 | GCA_001191565 | cladeA |
| *Lactobacillus paracasei* | L9 | GCA_001244395 | cladeA |

TABLE 2-continued

An overview of all publicly available genomes belonging to the *L. casei* group that were used in this study. If available, the strain name is given in the second column.

| *Lactobacillus* species | strain | accession number | clade |
| --- | --- | --- | --- |
| *Lactobacillus paracasei* | DSM 5622 | GCA_001436385 | cladeA |
| *Lactobacillus paracasei* | KL1 | GCA_001514415 | cladeA |
| *Lactobacillus paracasei* | L9D | GCA_001858275 | cladeA |
| *Lactobacillus paracasei* | LC-Ikematsu | GCA_001895185 | cladeA |
| *Lactobacillus paracasei* | RI-210 | GCA_001981715 | cladeA |
| *Lactobacillus paracasei* | RI-194 | GCA_001982085 | cladeA |
| *Lactobacillus paracasei* | RI-195 | GCA_001982095 | cladeA |
| *Lactobacillus rhamnosus* | ATCC 53103 | GCA_000011045 | cladeC |
| *Lactobacillus rhamnosus* | GG (ATCC 53103) | GCA_000026505 | cladeC |
| *Lactobacillus rhamnosus* | Lc 705 | GCA_000026525 | cladeC |
| *Lactobacillus rhamnosus* | HN001 | GCA_000173255 | cladeC |
| *Lactobacillus rhamnosus* | CASL | GCA_000226235 | cladeC |
| *Lactobacillus rhamnosus* | ATCC 8530 | GCA_000233755 | cladeC |
| *Lactobacillus rhamnosus* | R0011 | GCA_000235785 | cladeC |
| *Lactobacillus rhamnosus* | ATCC 21052 | GCA_000235865 | cladeC |
| *Lactobacillus rhamnosus* | LRHMDP2 | GCA_000311945 | cladeC |
| *Lactobacillus rhamnosus* | LRHMDP3 | GCA_000311965 | cladeC |
| *Lactobacillus rhamnosus* | CRL1505 | GCA_000414365 | cladeC |
| *Lactobacillus rhamnosus* | LOCK900 | GCA_000418475 | cladeC |
| *Lactobacillus rhamnosus* | LOCK908 | GCA_000418495 | cladeC |
| *Lactobacillus rhamnosus* | 2166 | GCA_000466865 | cladeC |
| *Lactobacillus rhamnosus* | LR231 | GCA_000508405 | cladeC |
| *Lactobacillus rhamnosus* | JCM 1136 | GCA_000615245 | cladeC |
| *Lactobacillus rhamnosus* | 51B | GCA_000699985 | cladeC |
| *Lactobacillus rhamnosus* | E800 | GCA_000712495 | cladeC |
| *Lactobacillus rhamnosus* | PEL5 | GCA_000712505 | cladeC |
| *Lactobacillus rhamnosus* | PEL6 | GCA_000712515 | cladeC |
| *Lactobacillus rhamnosus* | K32 | GCA_000735255 | cladeC |
| *Lactobacillus rhamnosus* | 24 | GCA_000743075 | cladeC |
| *Lactobacillus rhamnosus* | L34 | GCA_000784375 | cladeC |
| *Lactobacillus rhamnosus* | L35 | GCA_000784395 | cladeC |
| *Lactobacillus rhamnosus* | L31 | GCA_000784405 | cladeC |
| *Lactobacillus rhamnosus* | 116 | GCA_000801045 | cladeC |
| *Lactobacillus rhamnosus* | 308 | GCA_000814485 | cladeC |
| *Lactobacillus rhamnosus* | CLS17 | GCA_000932035 | cladeC |
| *Lactobacillus rhamnosus* | CNCM-I-3698 | GCA_001005625 | cladeC |
| *Lactobacillus rhamnosus* | Lr108 | GCA_001044025 | cladeC |
| *Lactobacillus rhamnosus* | 40f | GCA_001044405 | cladeC |
| *Lactobacillus rhamnosus* | 313 | GCA_001044415 | cladeC |
| *Lactobacillus rhamnosus* | 186_LRHA | GCA_001062885 | cladeC |
| *Lactobacillus rhamnosus* | 214_LRHA | GCA_001062955 | cladeC |
| *Lactobacillus rhamnosus* | 526_LRHA | GCA_001063655 | cladeC |
| *Lactobacillus rhamnosus* | 319_LRHA | GCA_001064515 | cladeC |
| *Lactobacillus rhamnosus* | 541_LRHA | GCA_001065365 | cladeC |
| *Lactobacillus rhamnosus* | 870_LRHA | GCA_001066715 | cladeC |
| *Lactobacillus rhamnosus* | 699_LRHA | GCA_001066975 | cladeC |
| *Lactobacillus rhamnosus* | 708_LRHA | GCA_001067025 | cladeC |
| *Lactobacillus rhamnosus* | 769_LRHA | GCA_001067215 | cladeC |
| *Lactobacillus rhamnosus* | 784_LRHA | GCA_001067335 | cladeC |
| *Lactobacillus rhamnosus* | 893_LRHA | GCA_001067625 | cladeC |
| *Lactobacillus rhamnosus* | 906_LRHA | GCA_001067885 | cladeC |
| *Lactobacillus rhamnosus* | 979_LRHA | GCA_001068015 | cladeC |
| *Lactobacillus rhamnosus* | 988_LRHA | GCA_001068045 | cladeC |
| *Lactobacillus rhamnosus* | 943_LRHA | GCA_001068195 | cladeC |
| *Lactobacillus rhamnosus* | 944_LRHA | GCA_001068215 | cladeC |
| *Lactobacillus rhamnosus* | DSM 20021 | GCA_001435405 | cladeC |
| *Lactobacillus rhamnosus* | ASCC 290 | GCA_001590655 | cladeC |
| *Lactobacillus rhamnosus* | R19-3 | GCA_001645615 | cladeC |
| *Lactobacillus rhamnosus* | Lrh8 | GCA_001656535 | cladeC |
| *Lactobacillus rhamnosus* | Lrh32 | GCA_001656545 | cladeC |
| *Lactobacillus rhamnosus* | Lrh31 | GCA_001656575 | cladeC |
| *Lactobacillus rhamnosus* | Lrh26 | GCA_001656605 | cladeC |
| *Lactobacillus rhamnosus* | Lrh23 | GCA_001656635 | cladeC |
| *Lactobacillus rhamnosus* | Lrh22 | GCA_001656655 | cladeC |
| *Lactobacillus rhamnosus* | Lrh20 | GCA_001656675 | cladeC |
| *Lactobacillus rhamnosus* | Lrh19 | GCA_001656685 | cladeC |
| *Lactobacillus rhamnosus* | Lrh15 | GCA_001656715 | cladeC |
| *Lactobacillus rhamnosus* | Lrh11 | GCA_001656735 | cladeC |
| *Lactobacillus rhamnosus* | Lrh34 | GCA_001656765 | cladeC |
| *Lactobacillus rhamnosus* | Lrh9 | GCA_001656785 | cladeC |
| *Lactobacillus rhamnosus* | Lrh7 | GCA_001656815 | cladeC |
| *Lactobacillus rhamnosus* | Lrh6 | GCA_001656835 | cladeC |
| *Lactobacillus rhamnosus* | Lrh5 | GCA_001656845 | cladeC |
| *Lactobacillus rhamnosus* | Lrh4 | GCA_001656875 | cladeC |

TABLE 2-continued

An overview of all publicly available genomes belonging to the *L. casei* group that were used in this study. If available, the strain name is given in the second column.

| *Lactobacillus* species | strain | accession number | clade |
|---|---|---|---|
| *Lactobacillus rhamnosus* | Lrh30 | GCA_001656895 | cladeC |
| *Lactobacillus rhamnosus* | Lrh28 | GCA_001656925 | cladeC |
| *Lactobacillus rhamnosus* | Lrh27 | GCA_001656945 | cladeC |
| *Lactobacillus rhamnosus* | Lrh25 | GCA_001656975 | cladeC |
| *Lactobacillus rhamnosus* | Lrh21 | GCA_001656995 | cladeC |
| *Lactobacillus rhamnosus* | Lrh18 | GCA_001657055 | cladeC |
| *Lactobacillus rhamnosus* | Lrh17 | GCA_001657075 | cladeC |
| *Lactobacillus rhamnosus* | Lrh16 | GCA_001657085 | cladeC |
| *Lactobacillus rhamnosus* | Lrh14 | GCA_001657115 | cladeC |
| *Lactobacillus rhamnosus* | Lrh13 | GCA_001657135 | cladeC |
| *Lactobacillus rhamnosus* | Lrh10 | GCA_001657165 | cladeC |
| *Lactobacillus rhamnosus* | Lrh33 | GCA_001657195 | cladeC |
| *Lactobacillus rhamnosus* | Lrh42 | GCA_001657205 | cladeC |
| *Lactobacillus rhamnosus* | LRB | GCA_001721925 | cladeC |
| *Lactobacillus rhamnosus* | HCT70 | GCA_001756565 | cladeC |
| *Lactobacillus rhamnosus* | ASCC 3018 | GCA_001831215 | cladeC |
| *Lactobacillus rhamnosus* | ASCC 3016 | GCA_001831225 | cladeC |
| *Lactobacillus rhamnosus* | ASCC 3029 | GCA_001831235 | cladeC |
| *Lactobacillus rhamnosus* | ASCC 1521 | GCA_001831275 | cladeC |
| *Lactobacillus rhamnosus* | RI-004 | GCA_001981725 | cladeC |
| *Lactobacillus rhamnosus* | AMC143 | GCA_001982425 | cladeC |
| *Lactobacillus rhamnosus* | AMC010 | GCA_001982435 | cladeC |
| *Lactobacillus rhamnosus* | BFE5264 | GCA_001988935 | cladeC |
| *Lactobacillus rhamnosus* | L156.4 | GCA_001991035 | cladeC |
| *Lactobacillus rhamnosus* | BPL5 | GCA_900070175 | cladeC |
| *Lactobacillus* sp. | FMNP02 | GCA_000814185 | cladeB |
| *Lactobacillus* sp. | HMSC17G08 | GCA_001807635 | cladeC |
| *Lactobacillus* sp. | HMSC072E07 | GCA_001809485 | cladeC |
| *Lactobacillus* sp. | HMSC068B07 | GCA_001809645 | cladeC |
| *Lactobacillus* sp. | HMSC064F12 | GCA_001809765 | cladeC |
| *Lactobacillus* sp. | HMSC077C11 | GCA_001809975 | cladeC |
| *Lactobacillus* sp. | HMSC078F07 | GCA_001810115 | cladeC |
| *Lactobacillus* sp. | HMSC066G01 | GCA_001812155 | cladeC |
| *Lactobacillus* sp. | HMSC068F07 | GCA_001812525 | cladeB |
| *Lactobacillus* sp. | HMSC061B07 | GCA_001812685 | cladeC |
| *Lactobacillus* sp. | HMSC073B09 | GCA_001813825 | cladeC |
| *Lactobacillus* sp. | HMSC075D02 | GCA_001814335 | cladeC |
| *Lactobacillus* sp. | HMSC056D05 | GCA_001814405 | cladeC |
| *Lactobacillus* sp. | HMSC073D04 | GCA_001815435 | cladeC |
| *Lactobacillus* sp. | HMSC25A02 | GCA_001816065 | cladeA |
| *Lactobacillus zeae* | KCTC 3804 | GCA_000260435 | cladeB |
| *Lactobacillus zeae* | DSM 20178 | GCA_001433745 | cladeB |

Phylogeny

Figure 8:
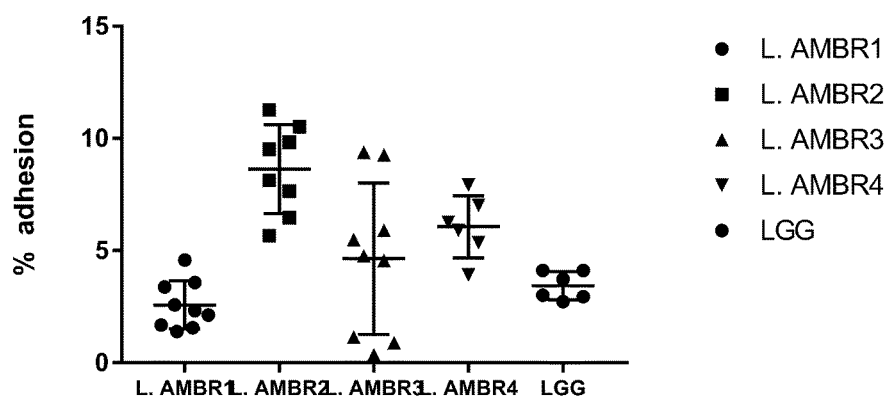
FIG. 8: Adhesion capacity of different *Lactobacillus* strains and *L. rhamnosus* GG to Calu-3 airway epithelial epithelial cells.
Figure 9:
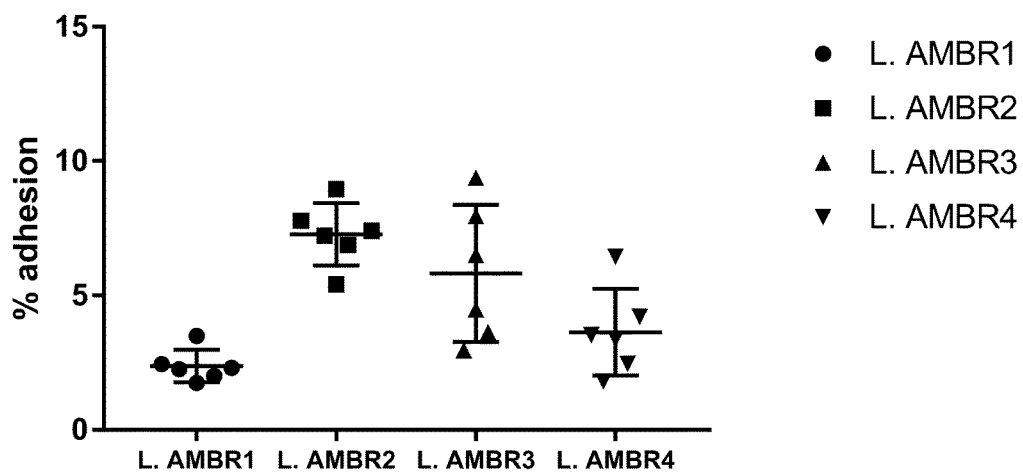
FIG. 9: Adhesion capacity of different *Lactobacillus* strains to VK2 E6/E7 vaginal epithelial cells

In order to study the genetic relatedness of the genomic assemblies, we constructed a high-quality maximum likelihood phylogenetic tree of the *L. casei* group using 776 core Cluster of Orthologous Groups (COGs). These COGs contain genes with at least 70% blastp identity and a presence in minimal 96% of the studied genomes. In addition, the genome of *Lactobacillus nasuensis* JCM 17158 (GCA_001434705) was added to the alignment to serve as an outgroup. This strain was chosen because it has the best quality assembly out of three strains that are closely related to the *L. casei* group (Sun et al., 2015). The resulting tree is shown in FIG. 8. The tree structure reveals three separate clades, with very small branch lengths within each clade in comparison to the branch lengths between the clades. Clade A contains the majority of the *L. casei* genomes and all of the *L. paracasei* genomes, as well as one unclassified L. sp. assembly. Clade B contains the two *L. zeae* genomes, five *L. casei* genomes (including the *L. casei* type strain ATCC 393), two unclassified lactobacilli, and our new URT isolate (*L. casei* AMBR2). Interestingly, all of these members are also the ones with an elevated GC content as shown in FIG. 18. Finally, clade C consists of all *L. rhamnosus* genomes as well as the remaining 12 L. sp genomes.

Pairwise Genome Comparison

In the current era of whole-genome sequencing, pairwise genome comparison metrics are often used as an operational method to detect species boundaries. Richter and Rosselló-Mora (2009) suggest the use of the average nucleotide identity (ANI) metric for prokaryotic species delimitation, possibly in combination with the TETRA metric. ANI is based on pairwise alignment of open reading frames or genomic fragments. The TETRA metric is the correlation between tetranucleotide frequencies in two genomes.

Figure 10:
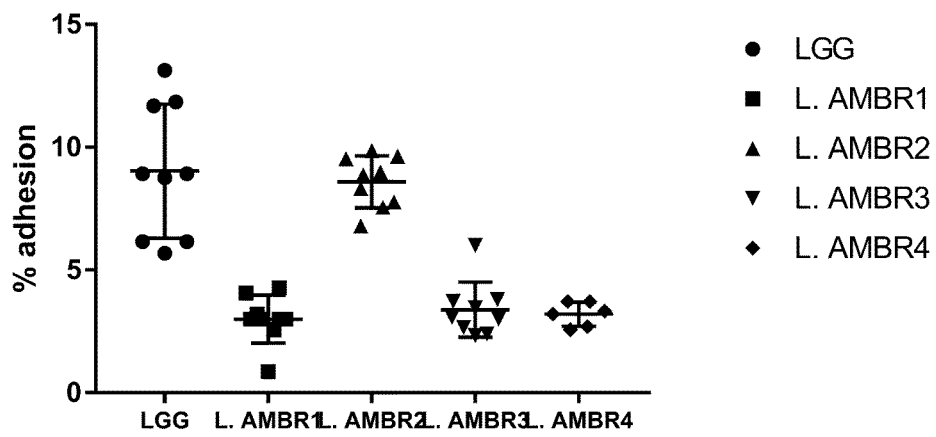
FIG. 10: Adhesion capacity of *L. casei* strains and *L. rhamnosus* GG to Caco-2 gut epithelial cells FIG. 11 Adhesion capacity of *L. casei* strains and other related lactobacilli on Calu-3 airway epithelial cells
Figure 11:
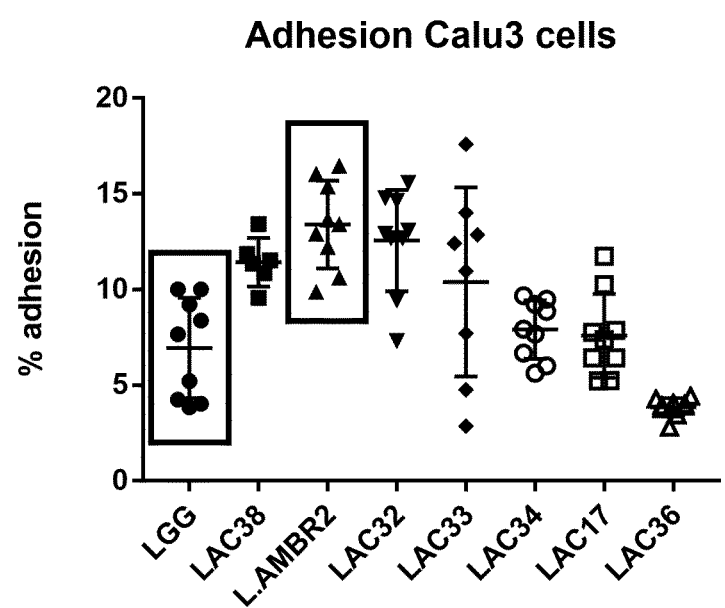
Figure 12:
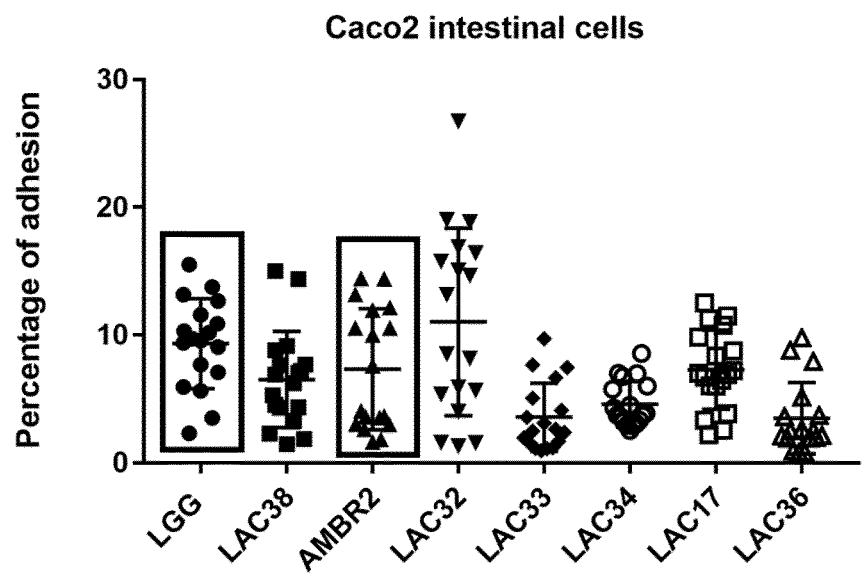
FIG. 12: Adhesion capacity of *L. casei* strains and other related lactobacilli on Caco-2 intestinal epithelial cells (A) and VK2/E6E7 vaginal cells (B).
Figure 12:
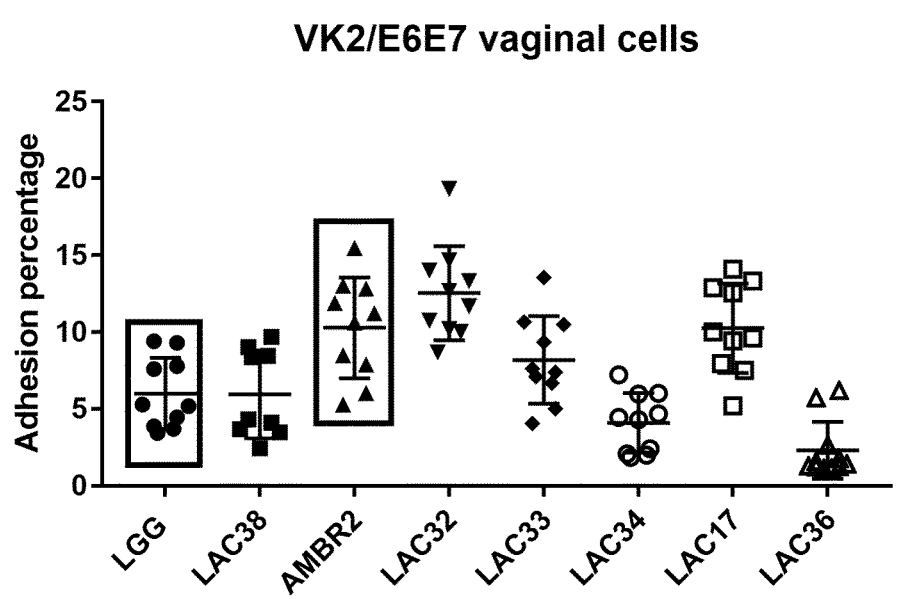

FIG. 10 shows the ANIb (ANI calculated using a blast implementation) and TETRA distances between all *L. casei* group genomes. The genomes are shown in the same order as in the phylogenetic tree. Both distance metrics support the grouping of the genomes in the three clades defined by the phylogenetic tree in FIG. 17. For species delimitation, Richter et al. (2009) advise an ANI cutoff value of 95-96%, although they remark that values of 94-95% within a species are also not uncommon. We observed a minimum ANI value of 96.05% in Clade A, 93.64% in Clade B and 96.26% in Clade C, suggesting that these three clades can be viewed as three separate bacterial species. This conclusion is also supported by very high TETRA values within each clade; 0.9941 or higher in clade A, 0.9872 or higher in Clade B and 0.9882 or higher in Clade C.

Gene Content

As described above, the *L. casei* group consists of 776 core COGs, which were used to build the phylogenetic tree. In addition, we identified 16,636 accessory COGs and an average number 2,786 genes per genome.

Since the GC-content (FIG. 18), phylogenetic tree (FIG. 17) and the ANI-values (FIG. 19A) all support the grouping of three different clades, we calculated the core and accessory genome of each clade using roary (Page et al., 2015). When comparing clades A, B and C, there seem to be no large differences in average number of genes per genome (Table 3). However, clade C seems to have an elevated number of core genes compared to clade A and B. The number of accessory genes is smallest for Clade B, which also has the smallest number of genomes. Clade A has the largest accessory genome while clade C is most abundantly represented in our data.

TABLE 3

Overview of the three clades defined by the phylogenetic tree. A core gene is defined as a gene present in more than 96% of the genomes.

| clade | number of genomes | genes per genome | genes in core genome | genes in accessory genome |
|---|---|---|---|---|
| Casei Group | 184 | 2,786 ± 133 | 776 | 16,636 |
| Clade A | 70 | 2,744 ± 125 | 1,878 | 5,398 |
| Clade B | 10 | 2,708 ± 116 | 1,874 | 2,349 |
| Clade C | 104 | 2,667 ± 82 | 2,070 | 4,014 |

Functional Capacity
Respiratory Potential

The results above show that our novel URT isolate, *L. casei* LMG P-30039 (AMBR2), belongs to the smaller clade B of the *L. casei* group. Interestingly, all members of this clade show an elevated GC content compared to the rest of the *L. casei* group. In addition to AMBR2, this clade contains the two *L. zeae* assemblies, two unclassified *Lactobacillus* species and five *L. casei* genomes, including the *L. casei* type strain ATCC 393 and the respiration-competent strain *L. casei* N87 (Zotta et al., 2016).

Since *L. casei* LMG P-30039 (AMBR2) was isolated from the upper respiratory tract of a healthy person, which is not a typical anaerobic fermentation niche, and since the respiration-competent strain *L. casei* N87 clusters within the same clade, we evaluated the respiratory potential of clade B together in relation to the other members of the *L. casei* group. Therefore, we screened the genomes for the presence of the cydABCD operon, encoding cytochrome bd oxidase, the only known terminal oxidase in the electron transfer chain of lactic acid bacteria (Pedersen et al., 2012; Ianniello et al., 2015). We found this operon to be present in all *casei* group members, suggesting that they are all genetically equipped with a minimal respiratory mechanism. In addition to this core respiration component, we evaluated the presence of other accessory respiration components (as described in Pedersen et al., 2012). Based on homology searches we were not able to find genes encoding heme uptake (fhuDBAR operon), heme efflux (hrtRBA operon and pefAB/pefRCD operon), heme degradation (yfeX orthologues) and menaquinone biosynthesis (menFDXBEC operon). However, an ortholog of the *Streptococcus agalactiae* alkyl hydroperoxide reductase (AhpC) was identified in all studied genomes, which is proposed to be a heme-binding protein, protecting intracellular heme from degradation (Pedersen et al., 2012; Lechardeur et al., 2011). These results indicate that *L. casei* AMBR2 is capable of respiration, like all members of the *L. casei* group.

Oxidative Stress Resistance

Respiration comes with an increase in oxidative stress. Since all *L. casei* group members are genetically equipped for respiration, we evaluated whether the different clades show different stress mechanisms for coping with oxidative stress.

The antioxidant superoxide dismutase (SOD) which scavenges $O_2^-$ into $O_2$ and $H_2O_2$ was long believed to be absent in the *Lactobacillus* genus. However, genome analysis recently revealed the presence of SOD genes in *L. casei* and *L. sakei* (Liu et al., 2011; Zotta et al., 2014). Therefore, we screened the whole *casei* group for SOD genes, revealing them to be only present in clade A strains (69 out of 70 genomes). Interestingly, mapping to four different SOD Pfam families (PF00080, PF00081, PF02777, PF09055) using Hmmer, lead to two different hits, one expected hit with PF00081 representing the iron/manganese SOD (found in 69/70 clade A genomes) and one rather unexpected hit with the copper SOD (4/70 clade A genomes), which is the SOD most commonly used by eukaryotes. The copper SODs are all annotated as hypothetical proteins and inspection using a genome browser showed that they are found on small contigs, surrounded by transposases.

Catalase, which catalyses the decomposition of $H_2O_2$ to H and $O_2$, also plays an important role in protecting the cell against oxidative stress. While the *Lactobacillus* genus is defined as catalase negative, recent studies have shown catalase activity in several strains including the respiration-competent strain *L. casei* N87. Therefore, the presence of catalase genes was evaluated within the whole *casei* group. Interestingly, ORFs annotated as catalase genes were identified only in strains belonging to clade B, and in one single genome of clade C. Two different types were found, one annotated as heme-catalase (length=1461 bp), the other one as a manganese catalase (length=807 bp). The heme-catalase gene was found in all 10 genome assemblies of clade B, while the manganese catalase gene was present in only 7 out of 10 clade B genomes.

In addition, two genes were annotated as catalase in one clade C strain (*Lactobacillus rhamnosus* CRL1505). One of the two ORFs showed a remarkable high sequence similarity with the first part of the heme-catalase gene identified in all clade B genomes, while the other gene showed high similarity with the second part of the heme-catalase gene. Visualization in a genome browser revealed that both genes lay directly next to each other, suggesting that it used to be a full heme-catalase gene, but has been split into two separate coding sequences due to a frameshift.

Additional genes related to oxidative stress like thioredoxin reductase, NADH peroxidase were found in all *casei* group genomes. MutT, an 8-oxoG triphosphatase is also found in all studied assemblies. It hydrolyses 8-oxoGTP, the oxidised form of GTP, into 8-oxoGMP, thereby preventing the misincorporation of 8-oxoGTP into DNA during replication (Veen and Tang, 2015) which helps in reducing mutations due to oxidative stress. We found that all genomes contain 1 single copy of the MutT gene, while 7 out of 10 clade B members possess 2 different copies. Interestingly, these seven members are the same assemblies that harbour two catalase genes. All together these results suggest that the presence of a catalase gene is a unique trait of the phylogenetic separate clade B within the *casei* group, while SOD seems to be uniquely found in clade A.

The invention claimed is:

1. A method of protecting against nasal epithelial barrier disruption and/or treating oronasopharyngeal infections in a subject in need thereof, the method comprising endonasally administering to the subject an isolated bacterial strain of *Lactobacillus casei* AMBR2, the strain deposited under accession number LMG P-30039, wherein the strain comprises at least one catalase gene.

2. The method according to claim 1, wherein oronasopharyngeal infections comprise otitis media, pharyngitis, chronic sinusitis, acute sinusitis, rhinitis, flu, mucositis, caries, gingivitis, and halitosis.

3. The method according to claim 1, further comprising administering to the subject a probiotic bacterium that is different compared to *L. casei* AMBR2.

* * * * *